(12) United States Patent
Goncalves

(10) Patent No.: US 6,905,585 B2
(45) Date of Patent: Jun. 14, 2005

(54) AUTOMATED SYSTEM FOR HIGH-THROUGHPUT ELECTROPHORETIC SEPARATIONS

(75) Inventor: Antonio M. Goncalves, Elkins Park, PA (US)

(73) Assignee: Temple University of the Commonwealth System of Higher Education, Philadelphia, PA (US)

( * ) Notice: Subject to any disclaimer, the term of this patent is extended or adjusted under 35 U.S.C. 154(b) by 0 days.

(21) Appl. No.: 10/660,308

(22) Filed: Sep. 10, 2003

(65) Prior Publication Data

US 2004/0050699 A1 Mar. 18, 2004

Related U.S. Application Data

(60) Provisional application No. 60/442,635, filed on Jan. 24, 2003, and provisional application No. 60/409,797, filed on Sep. 11, 2002.

(51) Int. Cl.[7] .................. G01N 27/447; G01N 27/453
(52) U.S. Cl. ...................................... 204/466; 204/616
(58) Field of Search ................................ 204/616, 617, 204/618, 621, 466, 467

(56) References Cited

U.S. PATENT DOCUMENTS

| | | | |
|---|---|---|---|
| 3,062,731 A | 11/1962 | Durrum | |
| 3,674,678 A | 7/1972 | Post, Jr. et al. | |
| 3,715,295 A | 2/1973 | Tocci | |
| 3,751,357 A | 8/1973 | Rains | |
| 3,865,712 A | 2/1975 | Davies | |
| 3,984,298 A | 10/1976 | Haber | |
| 4,101,401 A | 7/1978 | Hoefer | |
| 4,111,784 A | 9/1978 | Dahms | |
| 4,146,454 A | 3/1979 | Haber | |
| 4,207,166 A | 6/1980 | Dahms | |
| 4,234,400 A | 11/1980 | Kaplan et al. | 204/461 |
| 4,391,688 A | 7/1983 | Hamelin | |
| 4,414,073 A | 11/1983 | Iwata et al. | |
| 4,415,418 A | 11/1983 | Turre et al. | |

(Continued)

FOREIGN PATENT DOCUMENTS

| | | | |
|---|---|---|---|
| EP | 0134622 | 3/1984 | |
| JP | 360154150 | 8/1985 | |
| JP | 02195249 A | 8/1990 | ......... G01N/27/447 |
| JP | 2001188061 A | 7/2001 | ......... G01N/27/447 |

OTHER PUBLICATIONS

CAPLUS abstract for "Polymeric separation media for capillary electrophoresis of nucliec acids," Electrophoresis (1997), 18(12 13), 2243–2254).*
JPO computer translation of JP 2001–188061.*
"Chemoelectronic Mobilization of Chemical Species in Low–Conductivity Fluids: New Electrokinetic Effect," Norman Haber, Proc.Natl. Acad.Sci. USA, vol. 79, pp. 272–276, Jan. 1982.
"Electromolecular Propulsion (EMP): A Rapid, Simple Method for Analyzing Dyes Used in Microscopy," Norman Haber, *Biotechnic & Histochemistry*, Williams & Wilkins, vol. 73, No. 2, pp. 59–69, Feb. 3, 1998.

*Primary Examiner*—Alex Noguerola
(74) *Attorney, Agent, or Firm*—Drinker Biddle & Reath LLP

(57) ABSTRACT

A cassette is disclosed for use in performing electrophoretic separations on a solid substrate. The cassette includes reservoirs for containing buffer, electrodes for receiving electrical current and a substrate support. The cassette is designed to connect with external fluid and electrical sources. A method of conducting electrophoresis separation in both one and two dimensions using a cassette is also disclosed. Furthermore, a novel apparatus for use in performing electrophoresis separation is disclosed. The apparatus is preferably of modular construction with a docking station for receiving a cassette.

104 Claims, 9 Drawing Sheets

U.S. PATENT DOCUMENTS

| | | | |
|---|---|---|---|
| 4,693,804 A | 9/1987 | Serwer | |
| 4,699,680 A | 10/1987 | Shiraishi et al. | |
| 4,735,697 A | 4/1988 | Burton | |
| 4,741,814 A | 5/1988 | Mayes et al. | |
| 4,874,490 A | 10/1989 | Hochstrasser | |
| 4,892,639 A | 1/1990 | Sarrine et al. | |
| 4,966,792 A | 10/1990 | Terai et al. | |
| 5,066,377 A | 11/1991 | Rosenbaum et al. | |
| 5,068,019 A | 11/1991 | Yoshida et al. | |
| 5,106,477 A | 4/1992 | Coleman | |
| 5,147,522 A | 9/1992 | Sarrine | |
| 5,180,480 A | 1/1993 | Mans | 204/644 |
| 5,190,629 A | 3/1993 | Sugihara et al. | |
| 5,228,970 A | 7/1993 | Foley | |
| 5,384,025 A * | 1/1995 | Blasband | 204/619 |
| 5,411,657 A | 5/1995 | Leka | |
| 5,441,104 A | 8/1995 | Ehr et al. | |
| 5,458,760 A | 10/1995 | Kozulic | |
| 5,464,521 A | 11/1995 | Bellon | |
| 5,472,589 A | 12/1995 | Jacobs | |
| 5,543,023 A | 8/1996 | Lugojan | |
| 5,569,369 A | 10/1996 | Leffler et al. | |
| 5,582,702 A | 12/1996 | Cabilly et al. | |
| 5,635,045 A * | 6/1997 | Alam | 204/462 |
| 5,637,202 A | 6/1997 | Harrington et al. | |
| 5,637,203 A | 6/1997 | Sarrine | |
| 5,709,788 A | 1/1998 | Chen | |
| 5,736,022 A | 4/1998 | Axelsson | |
| 5,773,645 A * | 6/1998 | Hochstrasser | 204/456 |
| 5,827,418 A | 10/1998 | Haven et al. | |
| 5,858,189 A | 1/1999 | Williams | |
| 5,865,974 A | 2/1999 | Cabilly et al. | |
| 5,865,975 A | 2/1999 | Bishop | |
| 5,888,369 A | 3/1999 | Tippins et al. | |
| 5,972,188 A | 10/1999 | Rice et al. | |
| 5,989,400 A | 11/1999 | Islam | |
| 6,027,628 A | 2/2000 | Yamamura et al. | |
| 6,036,831 A | 3/2000 | Bishop | |
| 6,093,296 A | 7/2000 | Soane et al. | |
| 6,123,821 A | 9/2000 | Anderson et al. | |
| 6,136,173 A * | 10/2000 | Anderson et al. | 204/461 |
| 6,139,709 A | 10/2000 | Scott | 204/619 |
| 6,146,511 A | 11/2000 | Slater et al. | 204/457 |
| 6,176,962 B1 * | 1/2001 | Soane et al. | 158/292 |
| 6,193,868 B1 | 2/2001 | Hsu | |
| 6,245,206 B1 | 6/2001 | Anderson et al. | |
| 6,274,089 B1 * | 8/2001 | Chow et al. | 422/101 |
| 6,342,143 B1 * | 1/2002 | Minden | 204/462 |
| 6,368,481 B1 | 4/2002 | Sowa et al. | |
| 6,374,684 B1 | 4/2002 | Dority | |
| 6,375,899 B1 | 4/2002 | Ackley et al. | |
| 6,379,516 B1 | 4/2002 | Cabilly et al. | |
| 6,454,925 B1 | 9/2002 | Nakanishi et al. | 204/603 |
| 6,485,623 B1 * | 11/2002 | Anderson | 204/466 |
| 6,499,499 B2 * | 12/2002 | Dantsker et al. | 137/1 |
| 6,592,735 B1 | 7/2003 | Meier et al. | 204/621 |
| 2001/0037940 A1 | 11/2001 | Shih et al. | |

\* cited by examiner

AUTOMATED SYSTEM FOR HIGH-THROUGHPUT ELECTROPHORETIC SEPARATIONS

CROSS-REFERENCE TO RELATED APPLICATION

The present application is related to and claims dual priority from the commonly assigned and co-pending U.S. Provisional Patent Application Ser. No. 60/409,797, filed Sep. 11, 2002 and U.S. Provisional Patent Application Ser. No. 60/442,635, filed Jan. 24, 2003, both incorporated herein by reference in their entirety.

BACKGROUND OF THE INVENTION

Gel electrophoresis is widely used to separate complex mixtures of molecular species, notably proteins, nucleic acids, DNA. There are principally two methods for performing an electrophoresis process: one-dimensionally and two dimensionally. In its simplest form, one-dimensional ("1D") gel electrophoresis typically involves: (1) placing the sample (s) to be separated along or near one edge of a separating gel slab (hereinafter referred to simply as a "gel"), (2) causing an electropheretic buffer in one well or reservoir to contact the edge where the samples are located and causing an electrophoretic buffer in a second well to contact the opposite edge of the gel, and (3) applying an electrical voltage difference (hereinafter referred to simply as a "voltage") to electrodes immersed in each well. The application of the voltage causes an electric field to be established in the gel. The electric field, in turn, causes the molecular species in each sample to migrate in the gel at different rates. The rate of migration is determined based on the molecular shape and/or charge of the molecular species, as well as the type of gel and buffer. After the migration is complete, a dying step may be performed wherein the separated molecular species are blotted onto a polyvinyiledene fluoride ("PVDF") membrane (a nylon membrane, in the case of nucleic acids) and are then revealed by staining with dye.

In recent years, the process involved in performing gel electrophoresis has been simplified considerably through the use of commercially available pre-cast gels. Prior to this, gels were manufactured as needed in the test labs. Since gels are typically very fragile, it is necessary to protect the gels during shipment from the manufacturer to the test lab, as well as while in storage. Many of the commercially available pre-cast gels are sold sandwiched between rigid protective plastic or glass plates, while some merely have a flexible plastic backing and are stored within vacuum-sealed bags. There are also some manufacturers who supply gels in cassettes. In the field of gel electrophoresis, the term "cassette" generally refers to a rigid structure that has a gel located within it. Such cassettes not only operate to protect the gel, but also provide a convenient mechanism for transporting the gel prior to, during and after the electrophoresis process.

The steps described above for conducting the electrophoresis process can be performed in either the vertical or horizontal direction. In vertical gel electrophoresis, the gel is typically placed within a cassette that is open at both ends. Each end is in fluid communication with a different well containing a buffer. One well is typically located above the cassette and the other below. The cassette frequently serves at least as part of one wall of the upper buffer well. The cassettes that are typically used in vertical electrophoresis processes contain only the gel (i.e., no buffers or electrodes). Thus, separate wells are necessary in the vertical gel electrophoresis to provide the source for the buffer and the electrodes for providing the voltage. U.S. Pat. Nos. 5,736,022 and 6,027,628 describe conventional cassettes for use in vertical gel electrophoresis.

Heat dissipation is a major problem during gel electrophoresis. As the electric current passes through the gel, the buffer and gel begin to heat up. As the heat increases, it has a deleterious effect on the gel. If the heat is not dissipated, the gel will begin to breakdown. Accordingly, much effort has been expended in recent years to develop cooling systems that dissipate the heat generated during the process.

U.S. Pat. No. 5,888,369 describes the incorporation of an external heat exchanger in a vertical gel electrophoresis apparatus for circulation and cooling of the buffer. The apparatus accommodates cassettes that function to separate the two buffer wells. Ports are formed in one of the buffer well walls for channeling the buffer to the heat exchanger for cooling.

In horizontal gel electrophoresis, the gel is oriented predominantly in the horizontal direction. There are two general types of horizontal gel electrophoresis arrangements. In the first arrangement, the gel is placed on a slab above the two buffer wells. Each end of the gel is in contact with a porous wick that has an end located within the buffer in a buffer well. The wick conveys a sufficient amount of buffer and electrical current from the buffer well up to the gel. In the second arrangement, the gel is submerged under a thin layer of buffer, which extends from one well to the other. This is typically called "submarine" gel electrophoresis since the gel is at least partially submerged.

U.S. Patent Application Publication No. 20010037940 describes a conventional cassette for use in a horizontal gel electrophoresis apparatus. The cassette again serves to separate the two buffer wells of the apparatus. This is essentially, a horizontal adaptation of the typical vertical apparatus. The cassette includes a gel that extends into two reservoirs internal to the cassette (which are initially empty). The two reservoirs are located on opposite sides of the gel. When the cassette is inserted into the horizontal gel electrophoresis apparatus, each cassette reservoir communicates through side openings with one of the buffer wells in the apparatus. The apparatus buffer wells contain the electrodes for supplying the voltage. As such, when the apparatus buffer wells are filled with buffer, the buffer flows into the cassette reservoirs through the side openings and contacts each end of the gel. After each electrophoresis process is run, the apparatus buffer wells are emptied manually and the cassette is then removed. The cassette's reservoirs must be separately emptied.

While gel electrophoresis has become ubiquitous in the molecular biology laboratory, it has remained a laborious and time-consuming process that has largely resisted automation because of the need for human intervention at various stages. These include not only filling and emptying the buffer wells, but also removing the gel, blotting the separated molecular species onto a membrane and then staining them. Some steps have been taken to minimize or eliminate some of the labor-intensive steps. For example, U.S. Pat. Nos. 3,715,295, 3,865,712, 5,582,702 and 5,865,974 describe self-contained cassettes that include a pre-cast gel, electrodes and buffer. These cassettes only require connection to a voltage source for operation. Such self-contained cassettes are sold by Invitrogen Corporation (Carlsbad, Calif.) under the E-Gel® trademark. By their very nature, such self-contained cassettes use small amounts of buffer and carry low currents when in operation, thus eliminating the need for a dedicated cooling system.

Two-dimensional ("2D") gel electrophoresis is an extremely powerful separation tool that is becoming an increasingly important first step in proteomic analysis. 2D gel electrophoresis typically involves: (1) a "first dimension" separation according to isoelectric point in a pH gradient gel, (2) transfer of the separated molecular species to a second gel, and (3) a "second dimension" separation according to molecular size along a direction perpendicular to that of the first separation. The need to use two different gels, and the complexity and variability of the transfer between them, make automation of 2D gel electrophoresis an even greater challenge than that of 1D gel electrophoresis.

One system for 2D separation is discussed in U.S. Pat. No. 4,443,319. The system disclosed in that patent uses a cassette that includes both the gel and the electrodes, and which is open for the admission of buffer. Provisions are made for a second gel and a second set of electrodes to be used when the cassette is used in a 2D gel electrophoresis. However, the steps involved in the disclosed system are rather cumbersome and must be performed manually.

Haber has developed a revolutionary electrophoresis technique (hereinafter referred to as the "Haber technique") that allows separations to be performed in as little as five minutes. U.S. Pat. Nos. 3,984,298 and 4,146,454 describe the Haber technique. In addition to the short cycle time, the Haber technique utilizes low amounts of current and a small volume of buffer. Specifically, the Haber technique uses less than one milliliter of buffer in each well and is operated with currents below 0.5 mA. As such, there is no need for a cooling system. The buffers used with this technique contain conductivity suppressants. Accordingly, most of the current is carried by the molecular species being separated, rather than by ions in the buffer as in conventional gel electrophoresis. The sample is placed near the middle of the separation substrate (hereinafter referred to simply as the "substrate"). When the current is applied, some molecular species migrate toward the anode while others migrate toward the cathode. This technique is also described in N. Haber, *Proc. Natl. Acad. Sci.*, 79, 272 (1982) and in N. Haber, *Biotechnology & Histochemistry*, 73, 59 (1998). An apparatus using this technique is sold by Haber Inc. (Bayonne, N.J.).

Unfortunately, the Haber technique has received little attention, perhaps because of the dearth of suitable substrates. Although Haber has used gels, cellulose and other substrate materials, most of his reported work used filter paper. The primary deficiency of filter paper is that the resulting resolution is limited by broadening from diffusion that takes place in the absence of an applied electric field.

A need therefore exists for a method, apparatus and cassette suitable for automated high-throughput electrophoretic separations on solid substrates that can take advantage of techniques that use small buffer volumes.

SUMMARY OF THE INVENTION

The present invention relates to a method for performing electrophoretic separations on a solid substrate. The method includes the automated supplying and removal of buffer or other liquids to/from a separation chamber or cassette, as well as the controlled application of electrical voltages. The automated procedure eliminates or reduces the need for human intervention once the separation protocol is selected and the process initiated.

It is contemplated that the process may optionally involve, after separation, contacting the substrate while still inside the cassette with one or more liquids for chemical or other treatment of the separated molecular species, such as dye staining; radio-, immuno- or other labeling; or enzymatic digestion. In one preferred embodiment, after each separation, the interior of the cassette is rinsed and dried with the substrate still inside in order to facilitate subsequent handling of the substrate and/or examination of the separation results.

The separation chamber of the invention is hereinafter referred to as a "cassette" irrespective of whether it is easily inserted into and removed from the apparatus. A cassette with a substrate located within it is hereinafter referred to as a "loaded cassette". The cassette of the invention includes at least one pair of reservoirs for holding buffer (hereinafter referred to as "buffer reservoirs"), each reservoir containing an electrode and each in contact with a section of the substrate (when loaded). The substrate is placed substantially between each pair of buffer reservoirs and in fluid communication with all buffer reservoirs. At least one external port connects each reservoir to liquid supply and waste containers. At least one external port is connected to each reservoir for venting air, either directly outside or to a gas recovery container, and/or for connecting each reservoir to a pressurization/depressurization system and/or a liquid waste container. At least one external electrical contact is connected to each electrode and used to connect to a voltage supply.

For 2D electrophoresis, the cassette of the invention includes a second set of reservoirs and electrodes positioned orthogonal to the first set. The second pair of electrodes is designed to generate an electric field perpendicular to that generated by the first pair. The electrodes are connected so that, at any one time, voltage may be applied to one pair of electrodes and not to the other.

The cassette of the present invention preferably includes an additional reservoir (hereinafter referred to as the "substrate reservoir") located between the two buffer reservoirs for 1D cassettes and between both pairs of buffer reservoirs for 2D cassettes, and separate from them. The substrate reservoir encloses most of the substrate and serves to rapidly saturate the substrate with buffer, dye solution and other liquids, or with gases.

The substrate may be loaded into the cassette with the sample already on it, or the cassette may have at least one opening (hereinafter referred to as a "sample port") on one of its faces through which the sample(s) is/are placed on the pre-loaded substrate. The cassette is preferably designed to be opened after separation to permit removal of the substrate and examination of the separation results. The empty cassette may be later reloaded with a fresh substrate and reused. Alternatively, at least part of one cassette face is transparent to permit examination of the separation results without having to open the cassette and remove the substrate, in which case the cassette may later be discarded with the substrate in it. The environmental advantage of the disposable cassette of the invention over those of the prior art is that the cassette of the invention can be made free of buffers or other chemicals when discarded.

Preferably, the cassette of the invention is easily inserted into and removable from ("docking" and "undocking") the apparatus in which the separation is conducted. In this case, the cassette includes fluid ports and electrical contacts, which readily connect to the corresponding fluid ports and electrical contacts on the apparatus. Such quick-connect systems are commonly used in a wide variety of liquid delivery, electrical and electronics applications. The substrate may thus be loaded into the cassette in advance and unloaded subsequently (or the cassette may be discarded) without tying up the apparatus.

Any suitable substrate may be used with the present invention. Including filter paper, nitrocellulose membranes and gels, such as those described in U.S. Pat. Nos. 3,984,298 and 4,146,454. In addition, various gels, preferably attached to plastic or other rigid or flexible backing are suitable for use with the present invention according to conventional gel electrophoresis techniques.

Various methods are also described herein for use with the different cassette embodiments disclosed. One method embodiment uses a continuously moving substrate roll or fan-fold passing through a pre-docked cassette.

For automated high-throughput separations, the method, apparatus and cassette of the invention are most advantageously combined with standard automated laboratory systems such as robotic stacking and conveying systems for cassette or substrate storage and supply, robotic pipettes for automated sample placement on substrates, and automatic separation scanning, digitizing, storing and processing systems for examination of the separation results.

The method, apparatus and cassette of the invention are most effective for separations requiring only small volumes of buffer. For example, three hundred 2D separations using the Haber technique as it is applied to the present invention (notably including dye staining) can be performed automatically, without human intervention once the process has been initiated, in less than one hour and consuming less than two litters of each buffer.

The foregoing and other features and advantages of the present invention will become more apparent in light of the following detailed description of the preferred embodiments thereof, as illustrated in the accompanying figures. As will be realized, the invention is capable of modifications in various respects, all without departing from the scope of the invention. Accordingly, the drawings and the description are to be regarded as illustrative in nature, and not as restrictive.

BRIEF DESCRIPTION OF THE FIGURES

For the purpose of illustrating the invention, the drawings show a form of the invention which is presently preferred. However, it should be understood that this invention is not limited to the precise arrangements and instrumentalities shown in the drawings.

DETAILED DESCRIPTION OF THE VARIOUS EMBODIMENTS

Figure 1:
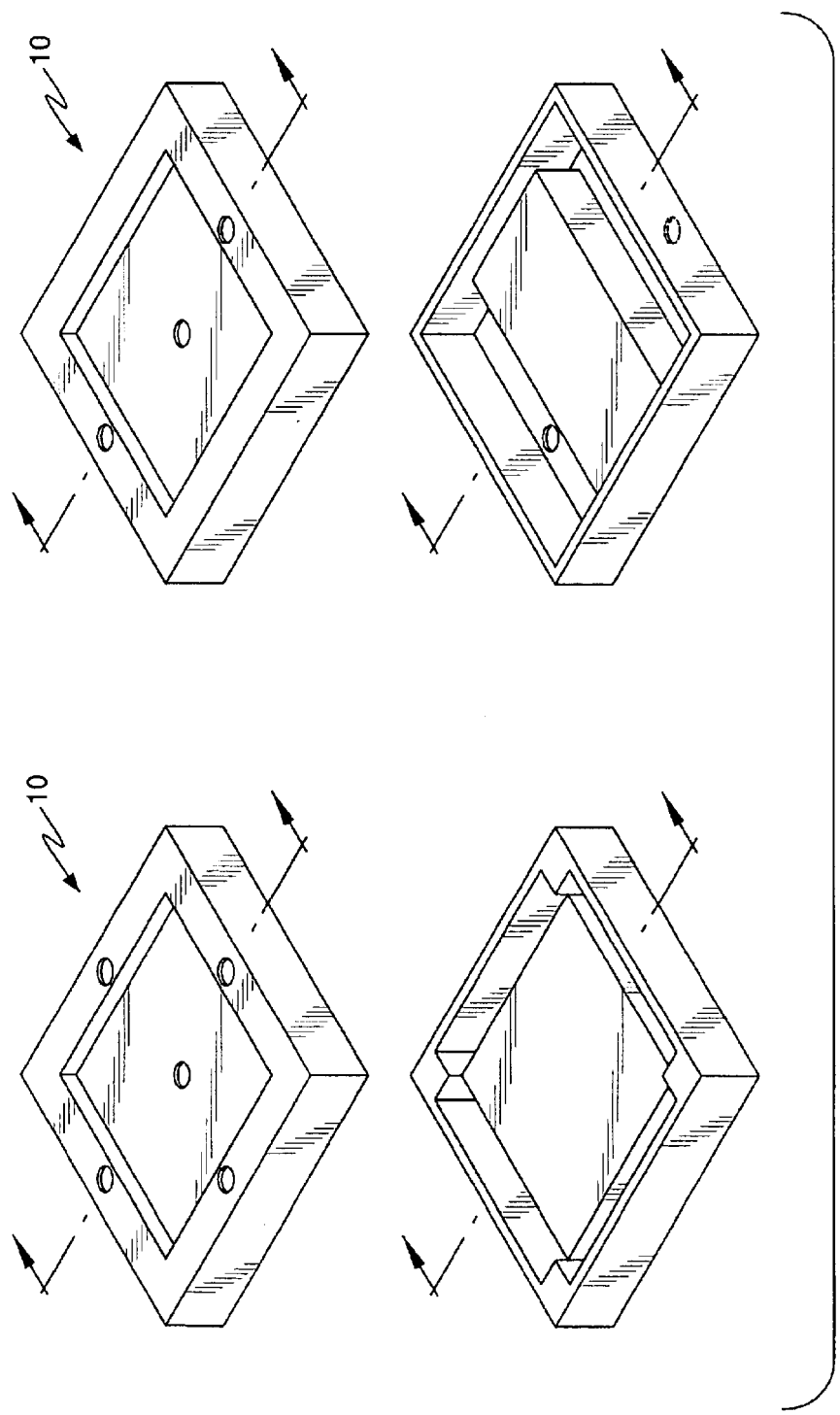
FIG. 1 illustrates exploded isometric views of 1D and 2D embodiments of a generic cassette according to the present invention.

The present invention pertains to a method, apparatus and cassette for performing automated electrophoretic separations on solid substrates, based primarily on the supply and removal of buffers and other liquids, and of electrical voltages, to and from a separation chamber (cassette), all without the need for human intervention once the separation protocol is selected and the process is initiated. Unless otherwise specified, the term "substrate" as used in this application is intended to encompass not only the substrate itself, but any backing or frame onto which the substrate may be disposed. Additionally, reference to a sample placed on a substrate is intended to include multiple samples placed on the same substrate.

The cassette of the invention is made largely from materials that are both electrically non-conducting and chemically resistant to the buffers used. For use with the Haber technique, the preferred materials include polytetrafluoroethylene ("PTFE", which is marketed by the DuPont Company under the trademark Telflon®), PVDF (commonly used in corrosion-resistant pipes and tubing), nylon, glass, or ceramin. Other materials may be used in the present invention, provided that any surface exposed to the buffers includes a coating of rugged, continuous, impermeable cladding of a chemically-resistant and electrically-insulating material such as PTFE, PVDF, glass or ceramic. Components that serve primarily for heat dissipation are advantageously made from glass-, ceramic- or PTFE-clad aluminum. For use with conventional gel electrophoresis techniques, the cassette can also be made from other materials commonly used with those techniques.

The substrate may be a gel of any type used in conventional gel electrophoresis. Alternatively, the substrate can be filter paper or any of the other substrate described in Haber. The substrates used in the Haber technique have the advantages of speed, low heat generation and low buffer usage. In order to facilitate handling, especially with an automated high-throughput operation as described below, the substrate is preferably attached to a backing or frame that provides rigidity for the substrate. There are other substrates that are currently being developed for protein microarray applications, such as the Hydrogel™ coatings being developed by PerkinElmer Life Sciences (Boston, Mass.), which may be used in the present invention.

As described below, the plane of the substrate is hereinafter referred to as the "XY plane", the direction of the first dimension separation is the "X direction", the direction of the second dimension separation is the "Y direction", and the normal to the plane of the substrate is the "Z direction". For simplicity, it is assumed that: (1) the cassette is shaped roughly like a parallelepiped, with two opposing surfaces (hereinafter referred to as "faces") being much larger than the other four (hereinafter referred to as "edges"); and (2) the faces of the cassette are parallel to the XY plane and are horizontal. Of course the cassette can take on a variety of different shapes and, thus, the exemplary shape described above is not to be considered limiting in any particular way. Similarly, the accompanying figures are intended only as schematic representations and, since component dimensions may differ by as much as two orders of magnitude, the figures are not drawn to scale in order to show some of the smaller dimensions more clearly. In addition, the figures do not shown some features that, albeit advantageous, only serve: (1) to guide, align or position various parts of the cassette with respect to each other; (2) to latch the cassette closed; or (3) to guide, align or position the cassette relative to the apparatus. These features, and their interaction with the cassette, would be readily apparent to those skilled in the art in light of the teachings provided herein.

The cassette of the invention docks into the electrophoresis apparatus through two fluid manifolds, one used primarily for liquids (hereinafter referred to as the "liquid manifold") and one used primarily for gases (hereinafter referred to as the "gas manifold"). The two fluid manifolds may be separate entities or may be combined in a single one. The cassette also connects to an electrical manifold in the apparatus. The electrical manifold may be a separate entity or may be combined with one or both fluid manifolds into a single entity. The manifolds are all controlled (preferably automatically) by the apparatus as described in more detail below. The fluid manifolds channel fluids between each cassette reservoir and associated fluid sources or waste containers on or connected to the apparatus. It is contemplated that, in addition to buffers and wash solutions, the liquids that may be supplied through the manifolds include those for treatment of the separated molecular species, such as dye staining; radio-, immuno- or other labeling; and enzymatic digestion. While buffers are required in the present invention, one for 1D separations and two for 2D separations, the use of additional buffers for running multiple separation protocols on different samples, or the use of wash or dye solutions or other post-separation treatment liquids is optional. Since dye staining is a very common post-separation treatment, the present specification references specifically the use of dye solutions and the process of dye staining. However, it should be readily apparent that one or more other post-separation treatments may be used, instead of or in addition to, the dye staining. Furthermore, treatment may be applied prior to or during the separation, so that it is possible to examine the progress of the separation while the separation progresses. For all purposes of this application, reference to post-separation treatment is deemed to include any treatment applied prior to or during the separation provided that the appropriate modifications in the sequence of the separation steps is made.

The first embodiment of the method of the present invention utilizes a closed detachable cassette that has been previously loaded with a fresh substrate, and includes the steps of: (1) placing a sample on the substrate through a sample port on the closed cassette and, if necessary, plugging the sample port; (2) docking the cassette; (3) supplying and removing fluids and voltages to and from the cassette to perform the separation and post-separation treatment; (4) undocking the cassette; (5) examining the separation results; and (6) discarding or recycling the used cassette. The used cassette may be recycled by unloading the used substrate and loading a fresh one. As described below, the cassette may include a transparent window to permit viewing of the processed substrate, although such transparent window is not necessary if the examination of the separation results is by a non-optical method such a radiography. Alternatively, following the separation and post-separation treatment, the cassette may be opened and the substrate removed for examination of the results directly, thereby eliminating the need for the cassette to have a transparent window for viewing the separation results.

For 2D separations, step 3 in the preceding paragraph preferably includes the following sub-steps: (i) admitting first buffer into the first dimension buffer reservoirs until the first buffer level is at least above the substrate and the first dimension electrodes; (ii) waiting until the substrate is saturated with first buffer; (iii) applying a voltage to the first dimension electrodes until the first dimension separation is completed, while (preferably) removing any first buffer that enters the second dimension buffer reservoirs through the substrate cross-section; (iv) substantially emptying the first dimension buffer reservoirs; (v) optionally, rinsing the first and second dimension buffer reservoirs and the substrate with wash solution; (vi) admitting second buffer into the second dimension buffer reservoirs until the second buffer level is at least above the substrate and the second dimension electrodes; (vii) waiting until the substrate is saturated with second buffer; (viii) applying a voltage to the second dimension electrodes until the second dimension separation is complete, while (preferably) removing any second buffer that enters the first dimension buffer reservoirs through the substrate cross-section; (ix) substantially emptying the second dimension buffer reservoirs; (x) optionally, rinsing all the reservoirs and the substrate with wash solution; and (xi) optionally, drying all reservoirs and the substrate with air or other gas.

Optionally, if post-separation treatment is desired, the following additional sub-steps are performed between sub-steps (x) and (xi): (a) admitting staining dye solution or other liquid for post-separation treatment into the first and/or second dimension buffer reservoirs; (b) waiting until staining or other post-separation treatment is completed; (c) substantially emptying the first and/or second dimension buffer reservoirs; (d) optionally, rinsing the first and/or second dimension buffer reservoirs and the substrate with wash solution. For 1D separations, sub-steps (vi) through (xi) are omitted; any optional post-separation treatment is performed after sub-step (v) in an analogous manner.

The above method is a preferred embodiment that may be used with a wide variety of cassettes. One embodiment of a cassette 10 for use in the method is shown schematically in FIG. 1, which is an isometric view of the cassette with its upper and lower portions shown separated. In this figure there is no substrate shown for clarity. Referring now to FIGS. 1A–1D, various cross-sectional configurations of the cassette are shown, each showing an alternative configuration taken along the section line in FIG. 1. Specifically, as shown in FIG. 1A, the cassette 10 includes an upper portion or cover 12 and a lower portion or body 14. The cover 12 and body 14 are designed to mate or seal together to form an enclosure. The combination of the upper and lower portions 12, 14 defines at least two spaced apart buffer reservoirs 16. As shown, each reservoir is formed by recessed cavities 18. While the illustrated embodiment shows recessed cavities in both the upper and lower portions, it is contemplated that only one portion (either the upper or lower) may include the recessed cavity 18.

At least one electrode 20 is mounted within each buffer reservoir 16. The electrode is located such that electrical current can be transmitted into a buffer located within the reservoir. Electrical leads (not shown) extend from the electrode to an electrical contact located on an external surface of the cassette 10.

Since a 2D cassette includes additional reservoirs that are orthogonal to the first set of buffer reservoirs, it should be readily apparent that a 2D cassette would look identical in cross-section to the cassette shown in FIG. 1A.

A substrate 22 is located on a substrate support 24 formed on the lower portion 14 between the two recessed cavities 18 in FIG. 1A. (Of course, in a 2D cassette, the substrate support 24 would extend between all recessed cavities in the lower portion 14.) A substrate cover 26 is preferably formed in the upper portion 12 between its associated recessed cavities 18. As will be discussed in more detail below, the substrate cover 26 and substrate support 24 are formed on (or attached to) the upper and lower portions 12, 14 such that the substrate cover 26 preferably substantially contacts the upper surface of the substrate 22 and the substrate support 24 substantially contacts the lower surface of the substrate 22, thereby sandwiching the substrate 22 between the two. In order to provide proper sealing without damaging the substrate 22, the interior walls 19U, 19L of the recessed cavities 18 must be configured such that the spacing formed between the interior walls 19U. 19L are spaced just enough to contact the substrate 22 when the upper portion 12 is sealed to the lower portion 14.

A sample port 28 is formed in the substrate cover 26 and provides a means for placing a sample on substrate 22 without opening the cassette 10. The location of the sample port 28 can be at any suitable position in the substrate cover 26, depending on the process to be run. The port in FIG. 1A is shown centrally located which is typically associated with 2D operations using the Haber technique (i.e., a single sample is placed roughly equidistant from all four electrodes.) For 1D operation with the Haber technique, multiple samples may be placed on a line parallel to the electrodes 20 and roughly midway between them, in which case the cassette has multiple sample ports 28 or may have an elongated slot. For conventional 2D gel electrophoresis techniques, the sample port 28 would be located so as to permit one sample to be placed near one corner of the substrate for 2D separations. For conventional 1D gel electrophoresis techniques, the sample port 28 would be located so as to permit multiple samples to be placed near one end of the substrate, roughly parallel to one of electrodes 20. Of course, the cassette can be configured without a sample port 28. However, in such cases, the substrate 22 would have to be loaded into the cassette with a sample already on it.

As discussed above, the substrate cover 26 and support 24 preferably contact the substrate. In addition to providing sealing, the contact serves to dissipate heat generated during the separation. In order to permit examination of the separation without opening the cassette, it is preferable that at least one of the cover 26 or support 24 include a transparent window (or be formed from transparent material.)

The cassette 10 preferably includes fluid ports 30 which communicate with each buffer reservoir 16. The fluid ports 30 supply and exhaust liquids from the buffer reservoirs 16. As shown, the fluid ports 30 are preferably formed in the bottom of the recessed cavity 18 on the lower portion 14. Although the ports 30 are shown centrally located, that is not a requirement. However, it is preferred that the cavities 18 be configured to facilitate flow of liquid to and from the ports 30 thereby providing for ease of filling and emptying of the reservoirs 16. As will be discussed in more detail below, the fluid ports 30 communicate with suitable supply and waste reservoirs in the associated electrophoresis apparatus.

The cassette 10 also preferably includes vent ports 32 which communicate with the buffer reservoirs 16. The vent ports 32 are preferably formed as openings into the recessed cavities in the upper portion 12. The vent ports 32 serve to release air displaced by buffer entering reservoirs 12, any evaporated buffer, or any gases generated during the separation. The vent ports 32 also permit air to be readmitted into reservoirs 16 when buffer is removed. To prevent liquid overflow through vent ports 32, a float or other one-way shut-off valve (not shown) may be incorporated into the upper portion 12. The vent ports 32 may vent directly to ambient or, preferably, are connected through a gas manifold to a gas recovery system. It is contemplated that pressurized air (or other gas) may be used to facilitate removal of buffer and cleansing of the cassette, and depressurized air to facilitate filling. In such cases the vent ports 30 are preferably connected through a gas manifold to a pressurization or depressurization source.

During operation of the cassette 10 in FIG. 1A, the buffer is channeled through fluid ports 30 into the reservoirs 16 until the buffer level reaches a desired level (shown by dashed lines B) which is above both substrate 22 and electrodes 20. After the separation, the buffer is exhausted through fluid ports 30 to a liquid waste system, while air or other gas is admitted through vent ports 32.

Alternatively, if one-way buffer flow is desired, either continuously or periodically, the process would be run with the buffer entering the reservoirs 16 through ports 30 and exiting through vent ports 32. In this variation of the invention, the vent ports 32 would need to connect to a liquid waste container. Buffer flow may also be in the opposite direction, i.e., with the buffer entering through ports 32 and exiting through ports 30, but this arrangement is less desirable.

As with the fluid ports 30, the vent ports 32 can be located at any suitable position to facilitate the electrophoresis operation, such as in the side walls of the upper or lower portions. Also, it may be desirable, depending on the configuration of the apparatus, to form the vent ports 32 such that they extend through the cassette walls or with external conduits to the bottom of the cassette, thus permitting supply of both liquids and gases from only one side of the cassette. Also, it should be readily apparent that the embodiment shown and described is intended for horizontal electrophoresis. However, the teachings provided herein are also applicable to electrophoresis with the cassette oriented vertically or in any other inclination, provided that ports 30 and 32 are appropriately located.

Figures 1A, 1B, 1C, 1D:
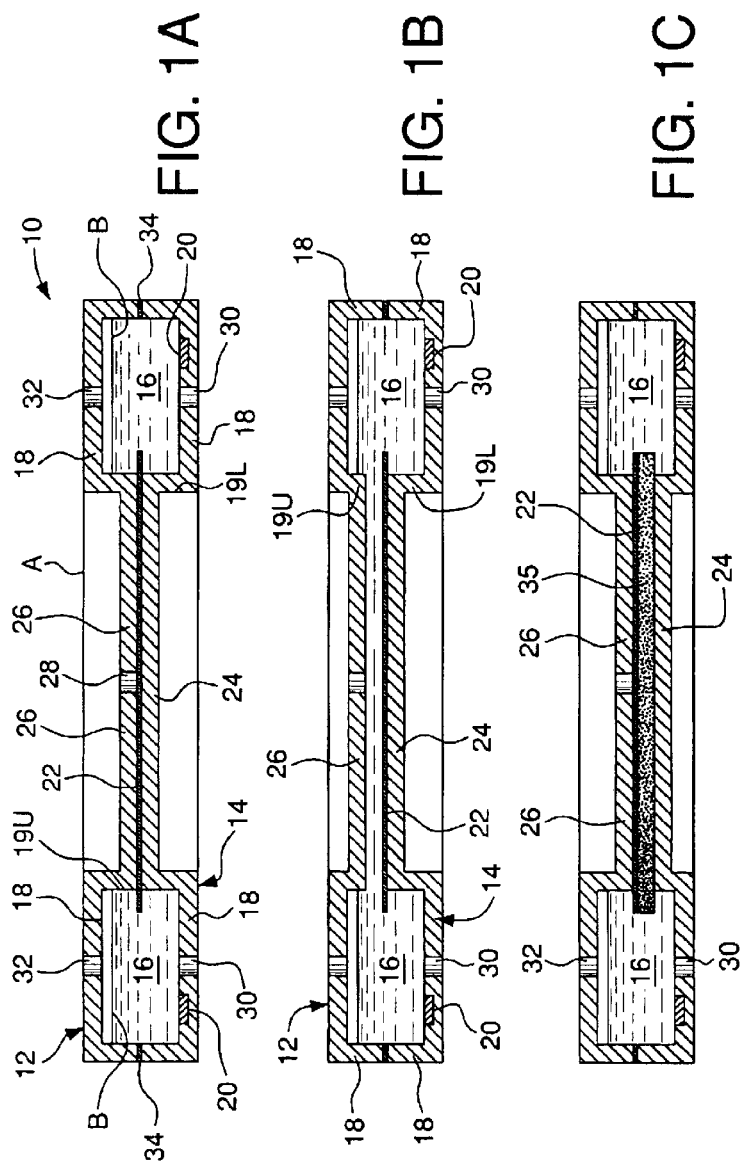
FIGS. 1A–1D illustrate various cross-sections of the cassettes of FIG. 1 according to different embodiments of the present invention.

As shown in FIG. 1, the cassette 10 is advantageously separable into two portions, to facilitate construction and permit convenient loading and unloading of substrate 22. The engagement of the portions is in a fluid-tight manner so as to prevent leakage of buffer. Preferably a continuous compression gasket 34, O-ring seal or other sealing device is located between the upper and lower portions 12, 14.

The upper portion or cover 12 may be connected to lower portion or body 14 in any convenient manner, such as with a hinge, fasteners or it can slide on grooves formed in the lower portion. Alternately, the upper and lower portions can be held together by mechanical pressure from the electrophoresis apparatus. It is also contemplated that the cassette may include a guide or alignment portion which mates with guide or alignment portions in the apparatus to permit proper docking of the cassette. In the cassette embodiment shown in FIG. 1A, the substrate 22 is saturated with buffer only through the small portions of the substrate 22 that extend into the buffer reservoirs 16. This lengthens preparation time considerably, an important consideration when using the Haber technique (which permits separations to be performed in each dimension in about five minutes). Therefore, if high throughput is desired, it is important to accelerate as much as possible any steps prior to and subsequent to the separation steps themselves.

Referring now to FIG. 1B, a second embodiment of the cassette 10 is shown. In this embodiment, the buffers reservoirs 16 are not separated. Instead, buffer is permitted to flow between the buffers over the top of the substrate. In this configuration, the interior walls 19U, 19L are sized so that a gap remains between the upper portion and the lower portion when they are sealed to one another. Thus, in use, the substrate 22 will be covered with a layer of buffer in a manner analogous to conventional submarine gel electrophoresis. The additional buffer increases the rate of diffusion into substrate 10. However, the additional buffer results in increased current passing through the layer of buffer above the substrate 22. The increased current contributes to the generation of heat during the process without furthering the separation process. This increased current is referred to herein as "unproductive current." In order to minimize the unproductive current (and, thus, minimize the unwanted development of unnecessary heat), it is desirable to make the buffer layer over the substrate as thin as possible. Furthermore, in this embodiment, sample port 28 serves to prevent air from becoming trapped under the substrate cover 26.

Referring now to FIG. 1C, an embodiment of the invention is shown which includes a porous layer 35, such as filter paper or sponge material, which is located between the substrate 22 and the substrate support 24. Alternatively, the porous layer 35 may be placed between the substrate 22 and substrate cover 26, or on both sides of substrate 22. The porous layer 35 serves to facilitate the flow of buffer into the substrate 22.

Referring now to FIG. 1D, a fourth cassette embodiment is shown. In this embodiment, the substrate 22 is larger and extends into and bends downward into the reservoirs 16. The ends of the substrate 22 are preferably secured at the bottom of buffer reservoirs 12 by ledges 36 or some other means. To ensure that buffer is not trapped behind ledges 36 and behind substrate 22 (where the latter meets the bottom of buffer reservoirs 12), both ledges 36 and substrate 22 have substantial openings that allow buffer to escape. In this cassette embodiment, the buffer is first admitted up to the level shown by the dashed lines identified by the letter B to allow it to form a layer of buffer over the substrate 22. At this point, the buffer reservoirs 16 (as well as the second dimension buffer reservoirs) are fluidly connected. After substrate 22 is saturated with buffer, the buffer level is lowered to the level shown by dashed lines identified by the letter C and then the separation process is initiated.

When using the embodiment of the cassette shown in FIG. 1D, the method described above is modified by adding the sub-steps (in both the 1D and 2D versions) of lowering the first buffer level to below the horizontal separation area of the substrate so that a sufficient amount of substrate is located within the buffer to permit electric current to flow from the buffer into the substrate.

It is also contemplated that, when using the embodiment of the cassette shown in FIG. 1D, the buffer may be admitted through sample port 28 and runs over substrate 22 down into the buffer reservoirs 16 until the buffer level is at the level shown by dashed lines C, and the separation proceeds with the buffer at that level.

Figure 2A:
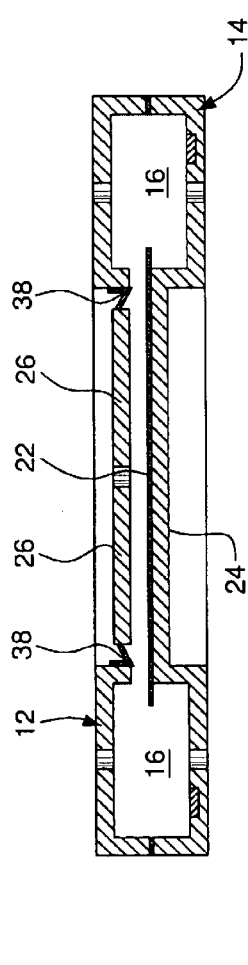
FIGS. 2A–2D illustrate additional cross-sectional variations of the cassettes of FIG. 1 according to alternate embodiments of the present invention.

Referring now to FIG. 2A, a preferred embodiment of the cassette 10 is shown. In this embodiment the entire periphery of substrate cover 26 is attached to the upper portion 12 through a fluid-tight hinge 38, which allows movement up and down of the substrate cover 26. During operation when no voltage is applied, the substrate cover 26 is generally located up and away from substrate 22. The buffer is then introduced, flowing across the top of the substrate 22 rapidly saturating the substrate 22. After saturation, the substrate cover 26 is located against the substrate 22, thus functioning as a heat sink while, at the same time, forcing any excess buffer from the top of the substrate 22. The hinge 38 preferably biases the substrate cover 26 away from the substrate 22. The substrate cover 26 is urged down against the substrate 22 by the apparatus when the voltage is applied. The substrate support 24 can likewise (or alternately) be attached to the lower portion through a hinge such that the support can be controlled to move toward and away from the substrate. The same result may be obtained by replacing the hinge with a gasket that provides a compression or sliding seal, in a manner similar to that described below.

Figure 2B:
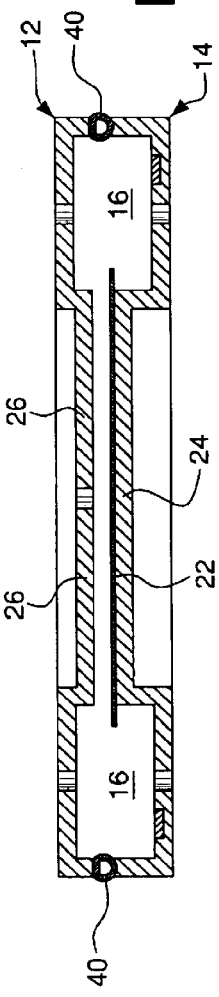

FIG. 2B illustrates a variation on the hinge embodiment described above. In this embodiment, the upper and lower portions 12, 14 are movable with respect to one another. This can be achieved by incorporating a compression seal 40, such as a high-compliance tube gasket (O-ring) or V-gasket, in place of the seal described previously. The flexibility of the seal permits variation in the spacing between the upper and lower portions while maintaining a fluid-tight seal. Thus, as in the embodiment shown in FIG. 2A, the initial spacing of the upper and lower portions 12, 14 is such that a layer of buffer is permitted to form over the substrate 22 to increase the speed of saturation. After saturation in complete, the upper and lower portions 12, 14 are compressed toward one another thereby eliminating the buffer on top of the substrate 22. Similar results can be achieved with the preferred arrangement shown in FIG. 2C where a sliding seal is incorporated between the upper and lower portions 12, 14. The sliding seal includes an O-ring gasket 42, with optional springs 44 to bias the upper portion 12 away from the lower portion 14.

Figure 2C:
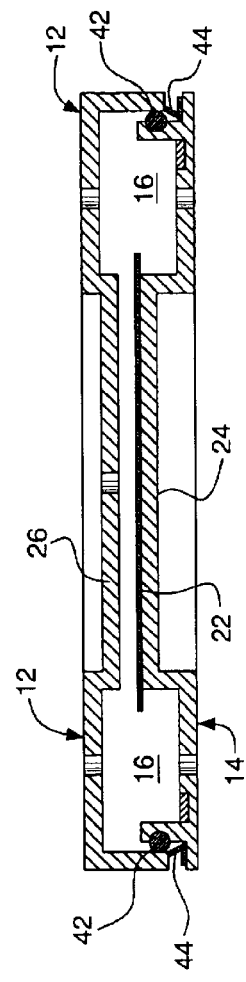

In the cassette embodiments shown in FIGS. 2A–2C, when those cassettes are configured for 2D separation (i.e., four buffer reservoirs), after the substrate 22 has been saturated with buffer and buffer layer above the substrate has been eliminated, buffer will still remain in all the buffer reservoirs 16, including the non-operating reservoirs. The buffer in the non-operating reservoirs can provide a path for unproductive current and thus increase heat dissipation. In order to minimize unproductive current and decrease the amount of heat dissipated, the non-operating buffer reservoirs are preferably emptied before voltage is applied for each separation. For example, when conducting the first dimension separation, the second dimension buffer reservoirs are emptied before voltage is applied. The buffer that is removed can be channeled to the appropriate buffer reservoirs 16 through the liquid manifold on the apparatus. A similar operation is undertaken before beginning the second dimension separation.

Figure 2D:
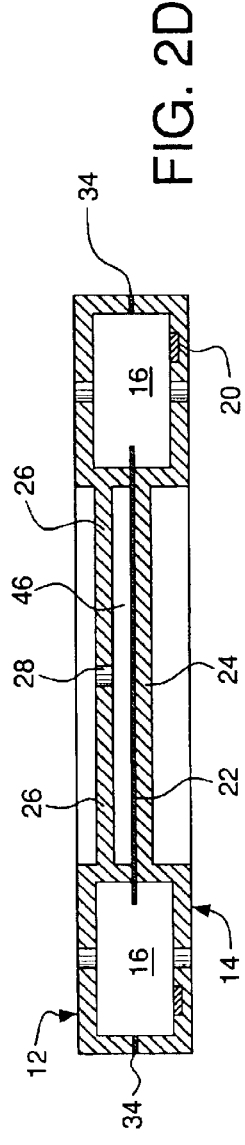

Referring now to FIG. 2D, another preferred embodiment of the cassette is shown which incorporates an additional reservoir 46 (hereinafter referred to as the "substrate reservoir") located above or below the central portion of the substrate 22. The substrate reservoir 46 communicates with the fluid manifolds through its own supply/exhaust and vent ports (not shown in the cross-sectional plane). The sample port 28 may also serve as the vent port for the substrate reservoir 46, or it may be plugged after a sample has been placed on the substrate 22.

The substrate reservoir 46 may be filled with the first buffer before, at the same time as or after the buffer reservoirs 16 are filled. Because of the large exposed surface of the substrate 22 within the substrate reservoir 46, the substrate 22 rapidly saturates. In addition to supplying the buffer to the substrate 22, the substrate reservoir 46 may also be advantageously used for saturating the substrate 22 with dye solution, rinsing off excess dye, and drying the substrate 22 prior to its removal or prior to examination of the separation results. In order to minimize unproductive current, the substrate reservoir 46 is preferably emptied prior to voltage application. In order to conserve buffer, the buffer can be channeled to the appropriate buffer reservoirs 16 through the liquid manifold on the apparatus, or internally through the cassette, rather than being discarded. Alternatively, the volume of buffer admitted into the substrate reservoir 46 can be limited to an amount sufficient to saturate substrate 22, with substantially no excess buffer left over.

When empty, substrate reservoir 46 provides poor thermal contact between the substrate 22 and the substrate cover 26. As such, this embodiment of the cassette relies primarily on the substrate support 24 for heat dissipation. In order to alleviate this deficiency an electrically insulating liquid may be introduced into the substrate reservoir 46 during voltage application. Such liquids are commonly used in high voltage transformer applications. The liquid should be selected so as to have a sufficient enough viscosity to prevent diffusion into the substrate 22.

Figure 3:
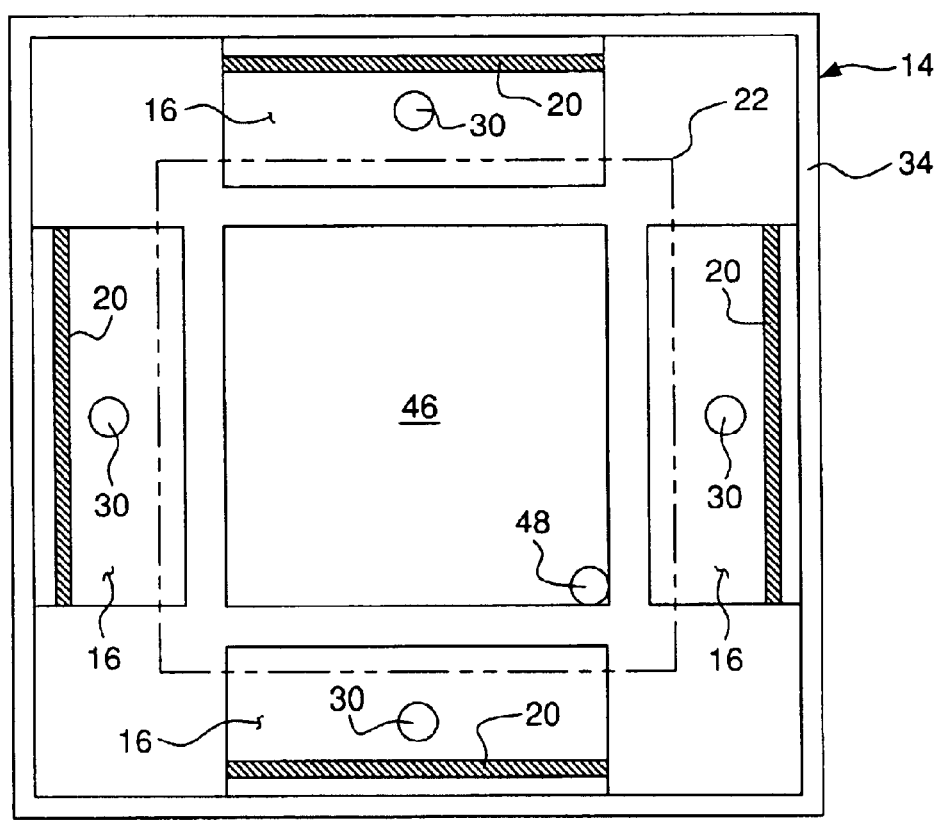
FIG. 3 is a top view of an open 2D cassette according to the embodiment shown in FIG. 2D.

While the two-part arrangement for the cassettes shown in FIGS. 1, 1A–1D and 2A–2D above is preferred, other practical arrangements are possible. For example, FIG. 3 is a top view of the body 14 of a 2D cassette according to the embodiment of the invention shown in FIG. 2D, with the substrate 22 shown in phantom but with the gasket 34 in place. As discussed above, this embodiment of the invention permits all liquid feeding and draining to occur from the bottom of the cassette. The first and second dimension buffer reservoirs 16 and the substrate reservoir 46 are shown with supply/exhaust ports 30 for the buffer reservoirs. Also shown is a preferred location for the supply/exhaust port 48 for the substrate reservoir 46. The substrate preferably has an opening formed in it to permit the fluid flow to and from the substrate reservoir 46 through the exhaust port 48 below. The electrodes 20 extend into the recessed cavities in the body 14 with the electrical connectivity being provided through the bottom wall of the body 14. Preferably, electrical contacts are formed on the bottom, outer surface of the cassette which are designed to align with and contact, when the cassette is docked, corresponding electrodes in the electrical manifold, which in turn connect to a power source in the apparatus. The electrodes 20 can be positioned anywhere inside the respective buffer reservoirs as long as they are covered with buffer during the separation. A 1D cassette would be similar to that shown except that the second set of buffer reservoirs 16 and associated electrodes 20 would be eliminated.

It is contemplated that the substrate 22 may be cross-shaped, with one branch extending into each buffer reservoir 16, irrespective of the shape of any backing to which it may be affixed (e.g., a cross-shaped substrate attached to a square backing). Alternatively, if the substrate 22 covers the entire surface of body 14, the gasket 34 is not needed if the substrate 22 can be compressed at the periphery to provide a fluid-tight seal.

The size and shape of the cassette can be changed as needed depending on the volume of buffer needed. For example, the face dimensions of the cassette can be decreased by reducing the footprint of the buffer reservoirs and increasing their height. For example, for an 8 cm×8 cm substrate reservoir and 4 cm×8 cm buffer reservoirs, the cassette face minimum dimensions are 16 cm×16 cm. By decreasing the buffer reservoir footprint to 1 cm×8 cm (and increasing reservoir height from 1 mm to 4 mm) the minimum cassette face dimensions are reduced to 10 cm×10 cm. Alternatively, if a continuous flow of buffer is provided, both the footprint and the height of the buffer reservoirs can be reduced to a just one or two millimeters.

Figure 4A:
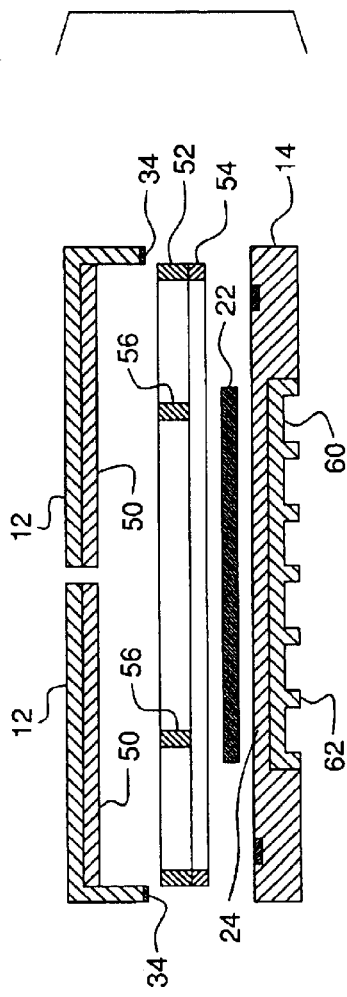
FIG. 4 illustrates additional cross-sectional variations of the cassette shown in FIG. 2D according to alternate embodiments of the present invention.
Figure 4B:
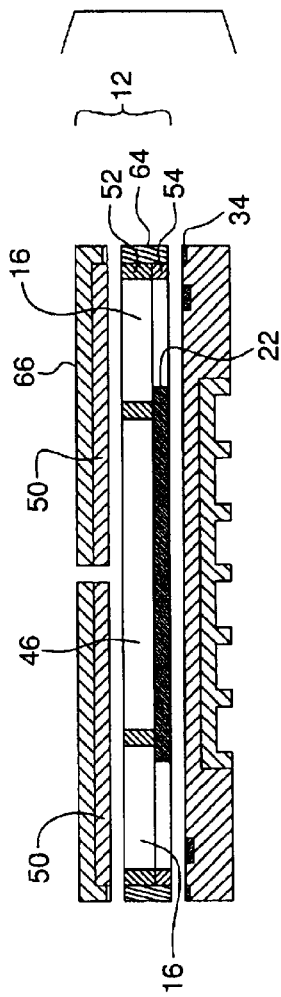
Figure 4C:
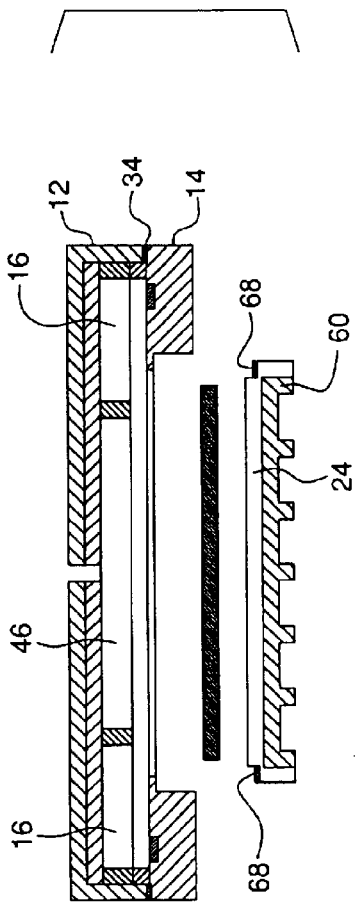

Although the cassette embodiments shown in FIGS. 1A–1D and 2A–2D illustrate the buffer reservoirs 16 extending both above and below the substrate 22, it is also contemplated that in applications where it is important to minimize the buffer volumes used (e.g., the Haber technique for large numbers of separations), the reservoir spaces below the substrate 22 may be eliminated. Referring to FIGS. 4A–4C, variations on the embodiment of the cassette illustrated in FIG. 2D are shown which eliminate the recessed cavity in the body 14. Those skilled in the art would be readily capable of making similar changes to the other cassette embodiments (other than the embodiment of FIG. 1D) in light of the teachings herein.

Figure 5:
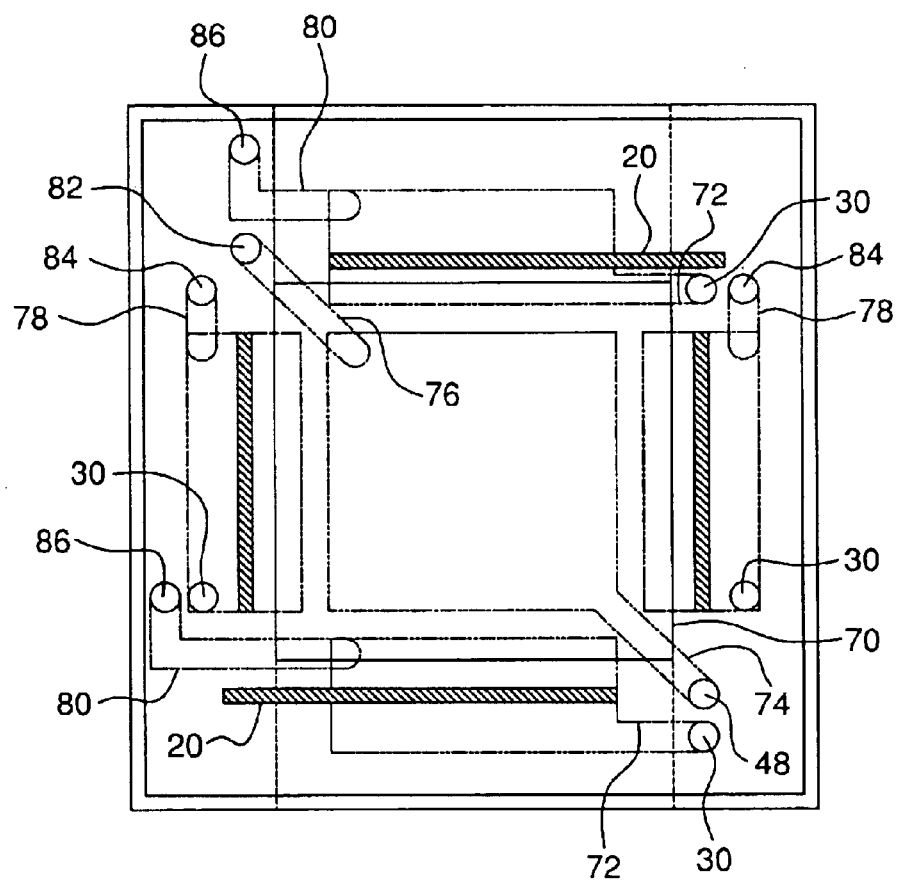
FIG. 5 is a top view of the body of a 2D cassette according to the modified embodiment of FIG. 4C.

FIG. 4A shows the cassette of FIG. 2D modified such that all the reservoirs are at or above the level of the substrate 22 in order to minimize the buffer volume used. Also, the venting is redirected to the bottom face of the cassette in order to allow gas recovery as well as pressurization of the reservoirs from one side only, thus permitting the cassette to be used in a simpler docking configuration. With the cover 12 raised, the substrate 10 is free to move on the top surface of body 14, thus facilitating automated loading. Since both supply/exhaust and vent ports now are all located on the body 14, they are not visible in FIG. 4A, but are illustrated in FIG. 5.

FIG. 4A also illustrates how the cover 12 can be conveniently fabricated using three compressible sheet gaskets 50, 52 and 54, which are preferably held by friction inside cover 12. Since they only need to be a few millimeters high, reservoirs 16 and 46 can be formed by cut-outs in a single sheet gasket 54, with walls 56 (which join out of the plane of the figure) separating them. While one gasket 54 is shown, it is also contemplated that multiple gaskets can be used to form the necessary reservoir height. In order to permit venting through the bottom, gasket 50 has horizontal cut-out channels proximal to the vent opening in each reservoir which extend downward, traversing gaskets 52 and 54 and the body 14, and terminating on the bottom face of the cassette. None of the cut-outs in gasket 50 are shown in FIG. 4A since they are out of the plane of the cross-section. They are, however, described in more detail with respect to FIG. 5. Alternatively, gasket 50, or all three gaskets 50, 52 and 54, is/are combined with cover 12 into a single molded piece of material or are otherwise formed from one piece of material.

Gasket 54, with a single large central cut-out section, serves three principal functions: (1) to compensate for the thickness of substrate 10 and permit gasket 52 to seal in a fluid-tight manner to the substrate 22 and the base 14, (2) to match the contour of the substrate 22 between reservoirs with no gaps connecting reservoirs, and (3) to assist in maintaining the position of the substrate 22 in the XY plane. The fit between the gasket 54 central cut-out and the substrate 22 is sufficiently loose for substrate 22 to be easily inserted, and the small gap between the two is sealed through compression of gasket 54 when the cassette is closed. Gasket 54 is not needed for thin substrates since gasket 52 can be compressed slightly more over substrate 22 than elsewhere. For much thicker substrates 22 or for substrates on backing or frames, compression of gasket 52 may not be sufficient to overcome the height of the substrate 22, and gasket 54 would then be necessary. Body 14 and cover 12 are sealed to one another by outer gasket 34, which is optionally an integral part of one of gaskets 50, 52 or 56. The height of cover 12 and the thickness of gasket 34 are configured such that, upon closure of the cassette, gaskets 52 and 54 are not compressed beyond what is needed to separate reservoirs 16 and 46.

A heat sink 60 may be included on the lower, external surface of the base 12, preferably under the substrate support 24. The heat sink 60 is preferably made from aluminum or similar material with high thermal conductivity. Cooling fins 62 may be added for increased heat transfer. Preferably, the substrate support 24 is formed as a very thin electrically insulating barrier for increased heat transfer. The bottom surface of the substrate support 24 may be coated with a high thermal conductivity paste to facilitate heat transfer to the heat sink 60. Alternatively, the substrate support 24 may be formed integral with the heat sink 60. In order to increase cooling, a fan or blower may be incorporated into the apparatus or cassette. It is also contemplated that, instead of a finned heat sink, the heat sink could be a thermoelectric cooling unit mounted in the apparatus or cassette. Another variation that is possible for the heat sink is the replacement of the cooling fins 62 with a cooling jacket within the heat sink 60 through which an externally cooled liquid is circulated. With some modifications of the arrangement shown, the cooling liquid may be buffer which is circulated from one of the buffer reservoirs 16. How much heat needs to be dissipated depends on the separation process being used. For example, a separation using the Haber technique typically generates on the order of 3 watts, which is low compared to other processes but is not negligible.

FIG. 4B shows a modification of the embodiment in FIG. 4A. In this embodiment, the bottom peripheral section 64 of the cover 12, where the substrate 22 and gaskets 52 and 54 are located, is detachable from the rest of the cover 66. The entire detached section (including the cover side portion 64, substrate 22 and gaskets 52 and 54) is free to move on the top surface of body 14, thus facilitating automated substrate loading.

Referring now to FIG. 4C, an additional modification is shown wherein the substrate support 24 and the heat sink 60 are detachable. As such, the opening thus formed permits a substrate to be inserted into the cassette and then the removed section placed back in. A seal 68, such as a compression gasket, is inserted between the substrate support 24 and the base 14.

The configuration of FIG. 4C also lends itself to modification of the embodiment shown in FIGS. 2B and 2C by the replacement of the seal with a high-compliance compression gasket (FIG. 2B), or a sliding seal (FIG. 2C), and the elimination of the central cut-out for substrate reservoir 16.

With respect to FIGS. 4A–4C, it is readily apparent that the electrodes 20 may, alternatively, be affixed to the substrate 22, or to its backing or frame, instead of being on the body 14. Or the electrodes 20 may be alternatively incorporated into the cover 12.

With respect to all of the cassette embodiments described above, particularly as shown in FIGS. 1, 1A–1D, 2A–2D and 4A–4C, it is assumed above, for simplicity, that the cassette separates into two pieces, a body and a cover, between which the substrate is placed. While such an arrangement is preferred because it has many practical benefits, particularly ease of construction of the cassette and ease of loading and unloading the substrate, other arrangements are also practical if less advantageous. Referring to FIG. 2D, for example, a 1D cassette is readily constructed in three parts: the left reservoir 16 excluding its right wall, the central section accommodating the substrate and including the right wall of the left reservoir 16 and the left wall of the right reservoir 16, and the right reservoir 16 excluding its left wall.

Referring now to FIG. 5, a top view of the body 14 of a 2D cassette according to FIG. 4C is shown. In the illustrated embodiment, the gasket 34 around the periphery and the detachable substrate support 24 and the heat sink 60 are removed, showing the opening defined by edges 70. The outlines of the buffer reservoirs 16 and the substrate reservoir 46, defined by the gasket 52 above, are shown for reference as phantom lines. For the substrate 22 to be loaded and unloaded without disturbing either the attachment of the body 14 to the cover 12 or the docking of the body 14 into the apparatus, all fluid ports and electrical contacts are channeled to locations outside the detachable section.

In addition, in order to facilitate loading the substrate 22 along the Y (lateral) direction, none of the connections with the apparatus are located either in front of or behind the detachable section. Thus, relative to FIG. 3, the supply/exhaust ports 30, 48 are redirected to the side, using channels 72, 74 formed in the gasket 52 (essentially extensions of the reservoirs). All the supply/exhaust ports traverse the body 14 downward to end on the bottom face of the cassette. In order to channel the vent ports to the bottom, horizontal channels 76, 78 and 80 are cut into gasket 50 above, connect to vent ports 82, 84 and 86 traversing gaskets 52 and 54 and the body 14. In addition, the locations of the contact areas are to the sides of the cut-out region, thus requiring the electrical connections to the electrodes 20 to be routed appropriately.

As shown in FIG. 5, each one of the channels leads to a different vent port 82, 84 or 86 on the bottom face of the cassette. Alternatively, the channels can be formed so as to converge to a single conduit which extends to one vent port on the bottom face of the cassette. This alternative is less forgiving of minor overfilling of reservoirs since they now communicate with one another through gasket 50 above.

As illustrated in the accompanying figures, the buffer reservoirs in each pair are not designed to communicate directly with one another. There are two principal reasons for this. First, it is sometimes desirable to have a different buffer in each of the buffer reservoirs 16 in each pair in order for the separation to take place in a buffer gradient (e.g., a pH gradient if each buffer has a different pH). Second, a buffer-filled channel connecting the buffer reservoirs 16 in each pair provides a path for unproductive current and adds to the need to dissipate heat. If the buffer reservoirs 16 in each pair connect only through the liquid manifold, the path is not only longer but is also interrupted during voltage application by two closed electrically-insulating valves. If heat dissipation and current handling capacity are not an issue, then the cassette and the liquid manifold can both be made simpler by connecting the supply/exhaust openings of both buffer reservoirs 16 in each pair inside the cassette.

Because of their substantially closed nature, the cassettes of the present invention can be operated vertically or with any other inclination provided that the arrangement of fluid ports is modified appropriately. For each reservoir, the supply/exhaust opening is preferably near the reservoir's lowest point so that substantially no liquid remains when the reservoir is emptied, while the vent opening is preferably near the highest point so that substantially no air is trapped when the reservoir is filled. Therefore, the inclination with which the cassette is to be operated dictates the location of the fluid openings for each reservoir. For horizontal operation, the fluid opening arrangement is not critical since all venting occurs above the top of all reservoirs. However, if the reservoirs are just a few millimeters high then even a relatively small unintended cassette inclination may have a significant effect. An easy solution is to purposely incline the cassette enough to ensure that the supply/exhaust and vent openings are always near each reservoir's highest and lowest points, respectively, even if the apparatus is not closely leveled. Preferably the inclination should be greater than ten degrees.

In addition to being operable horizontally, the 2D cassette of FIG. 5 meets all the requirements for operation with the edge at the top of the figure higher than the edge at the bottom of the figure (e.g., vertically). This is made possible by the upward direction of channels 76, 78 and 80, as shown, which permits complete filling of all reservoirs with the cassette oriented vertically. Alternatively, vent channels 76, 78 and 80 may all be directed, in a similar manner, to the same edge of the cassette for edge docking instead of face docking.

It is also contemplated that the method disclosed above may be practiced with a cassette that does not have the cover attached except while in operation, thus eliminating the need for openings for sample introduction or transparent faces for examination of the separation results.

Furthermore, the present invention may be practiced with a cassette that is docked but does not include a substrate (e.g., using the cassettes of FIGS. 4A–C). As such, the disclosed method would be modified to incorporate the steps of loading and unloading the substrate into and out of the cassette. It is not necessary for the cassette used in this embodiment to be easily detachable from the apparatus, except that it preferably is so as not to inhibit apparatus maintenance. Unlike the first method described above, the manner in which the substrate is loaded into the cassette is now especially important, particularly for automated operation.

If the cassette shown in FIG. 4A is used, the method involves the steps of (1) placing the sample on the substrate; (2) positioning the substrate on the body of the open cassette, with the cover raised and the body docked; (3) lowering the cover to close the cassette in a fluid-tight manner; (4) supplying and removing fluids and voltages to and from the cassette to perform the separation and post-separation treatment; (5) opening the cassette by raising the cover; (6) removing the substrate; (7) examining the separation results; and (8) discarding the substrate. It is also contemplated that the cover 12 may be preloaded with substrate 22, in which case the method would be modified accordingly and the cover could be reused after the process is complete.

If the cassette shown in FIG. 4B is used, the method would be varied to account for the fact that the substrate is located in the detachable side section of the cover. If the cassette shown in FIG. 4C is used, then the substrate is preferably loaded before it is placed within the cassette.

While the above cassettes provide for a second set of reservoirs for conducting 2D separation, it is also contemplated that 2D separation can be performed using a 1D cassette. In this embodiment, the method would be modified to include the following steps: (1) placing the sample on the substrate, (2) loading the substrate into the open pre-docked 1D cassette, (3) closing the cassette in a fluid-tight manner, (4) supplying and removing fluids and voltages to and from the cassette to perform the first dimension separation, (5) separating the appropriate moveable parts of the cassette sufficiently to permit rotation of the substrate, (6) rotating the substrate by ninety degrees around the Z axis passing through its center, (7) bringing together the appropriate moveable parts of the cassette in a fluid-tight manner, (8) supplying and removing fluids and voltages to and from the cassette to perform the second dimension separation and post-separation treatment, (9) opening the cassette, (10) removing the substrate, (11) examining the separation results, and (12) discarding the substrate. Of course, the method may be modified to use two in-line 1D cassettes which are oriented orthogonal to one another (in the Z-direction). In this embodiment, the substrate would be moved from one cassette to the other after the first separation is complete. Post-treatment can be performed either in the second 1D cassette or in a third cassette that includes only a substrate reservoir (no buffer reservoir or electrodes) if desired.

In the various methods described above, any suitable means may be used to position the substrate 22 or detachable side section (FIG. 4B) or bottom section (FIG. 4C), including (1) a set of rollers, preferably with the driving set in body and the free-running set in cover; (2) replacing the substrate support 24 above the heat sink 60 with an electrically insulating conveyer belt; or (3) having an external positioning arm move the substrate 22 into position and then withdraw. Alternatively, substrate 22 may be conveyed along the Y axis in continuous form, either in a roll or fan-fold, on one side of the cassette and taken up on the other side. In this embodiment, when the substrate is properly positioned, the conveyance of the substrate is stopped and that section of the substrate roll or fan-fold is pulled into the cassette until the separation is complete. For the cassette arrangement shown in FIG. 4C, a substrate 22 (or detachable side/bottom sections) may be readily translated horizontally without any fluid port or electrical connection interfering. If, as described below, cassettes are stacked on top of each other, the substrate 22 (or detachable side/bottom sections) can be loaded into each cassette without the other cassettes and their docking getting in the way.

In some embodiments of the apparatus in accordance with the present invention, the cassette may be inserted loosely into a receptacle and the apparatus, rather than the operator, automatically docks it into the fluid and electrical manifolds in order to ensure proper docking and less wear on the contact points. Optionally, at the start of each operation, the apparatus first locks the cassette in place and then tests each reservoir and port for leaks, and each electrical connection for discontinuities or shorts. If a fault is detected, the apparatus activates a visual and/or audible warning, unlocks the cassette and aborts the operation. Each operational step may be initiated by the operator at the appropriate time or, preferably, the entire order and timing of steps is programmed into the apparatus in advance and runs automatically once the separation protocol is selected and the operation is initiated.

All the methods described above are applicable to multiple cassettes docked in parallel, each using a separate set of fluid and electrical manifolds to connect to the apparatus. In this manner, each separation proceeds independently of the others, and one cassette may be docked and its operation initiated while another cassette is already in operation.

Also, the methods described above are applicable to separations performed using multiple interconnected cassettes, all cassettes using a single set of fluid and electrical manifolds. For example, the cassettes may be stacked on top of each other, with the connections between them being made fluid-tight. The cassette stack is essentially a single multi-substrate cassette, and all operational steps occur simultaneously for all substrates in the stack. Because air flow past each heat sink is reduced, forced air flow from a fan or blower may be desirable. If pre-loaded cassettes are used, the cassettes are disconnected from each other after each operation, and the operation is repeated each time with a new set of cassettes. Preferably, the cassette stack is permanent and a substrate, with a sample on it, is loaded into each cassette at the beginning of each operation as described above.

The cassette embodiments described above can be readily modified to permit stacking as described in the preceding paragraph. Referring to FIGS. 1 through 5, each one of electrodes 20 is made to connect to an additional electrical contact, on cover 12, aligned with the already described electrical contact on body 14, so that there is electrical continuity when multiple cassettes are stacked on top of each other. Also, the cassette of FIG. 3 may be used when multiple cassettes are operated horizontally requiring no modification to the fluid port arrangement. When the cassettes are stacked, vent ports of one cassette dock with supply/exhaust ports of the cassette above, except that the bottom cassette docks directly into the apparatus and the top cassette vents directly outside. The cassette stack thus has its reservoirs connected in series.Furthermore, the cassette of FIG. 5 may be used with multiple cassettes mounted vertically, requiring further that the supply/exhaust ports as well as the vent ports be extended to traverse the entire cassette face to face. When the cassettes are stacked vertically against each other, with the cover of one cassette against the body of the adjacent cassette, each set of supply/exhaust ports and each set of vent ports forms a continuous channel through the entire stack. The first cassette docks directly into the apparatus, and the last cassette is followed by a cover that terminates the continuous channels. The cassette stack thus has its reservoirs connected in parallel. Cassettes modified in this manner can also operate horizontally, stacked on top of each other in a similar manner.

In all cassette embodiments described above, it is also possible to stack multiple substrates, each with a sample already on it, directly on top of each other, and then simply insert the substrate stack into a single cassette, rather than using a separate cassette for each substrate as described in the preceding two paragraphs. However, such an arrangement is less desirable for two reasons: (1) saturating each substrate in the stack with buffer or other liquid is slowed unless the substrates are kept separated in order to permit the liquid to flow between substrates, and (2) the need to dissipate heat increases with the number of substrates since the heat transfer across the substrate stack is very inefficient.

The methods described above are especially suited to the rapid, automated operation of large numbers of cassettes or substrates sequentially or simultaneously, or in any combination of the two. Cassettes and substrates intended for automated operation preferably incorporate an identifier, such as a barcode. Pre-loaded cassettes are supplied, one at a time, from a storage bin to a robotic pipette that places a sample on each substrate. The cassette is then moved into position and docked. The separation and the post-separation treatment are performed and then the cassette is undocked and transferred through an automated reading and analysis system. After analysis is complete, the cassette is discarded or recycled. For use with unloaded pre-docked cassettes, substrates are supplied, one at a time from a storage bin to a robotic pipette that places a sample on each substrate. The substrate is then moved into position and loaded into an open pre-docked cassette and the cassette is closed. The separation and the post-separation treatment are performed, then the cassette is opened and the substrate is unloaded. The substrate is transferred through an automated reading and analysis system, after which the substrate is discarded.

The Haber technique typically uses less than six milliliters of each buffer in a 2D separation on an 8 cm×8 cm substrate, with each 2D separation taking less than 20 minutes (including dye staining). If an apparatus according to the present invention is used which accommodates ten stacks of ten cassettes each, then three hundred 2D separations can be performed automatically in one hour using less than two liters of each buffer. Since each separation requires less than 1 mA of current, one hundred simultaneous separations require no more than 100 mA, which standard laboratory power supplies are readily capable of handling.

Figure 8:
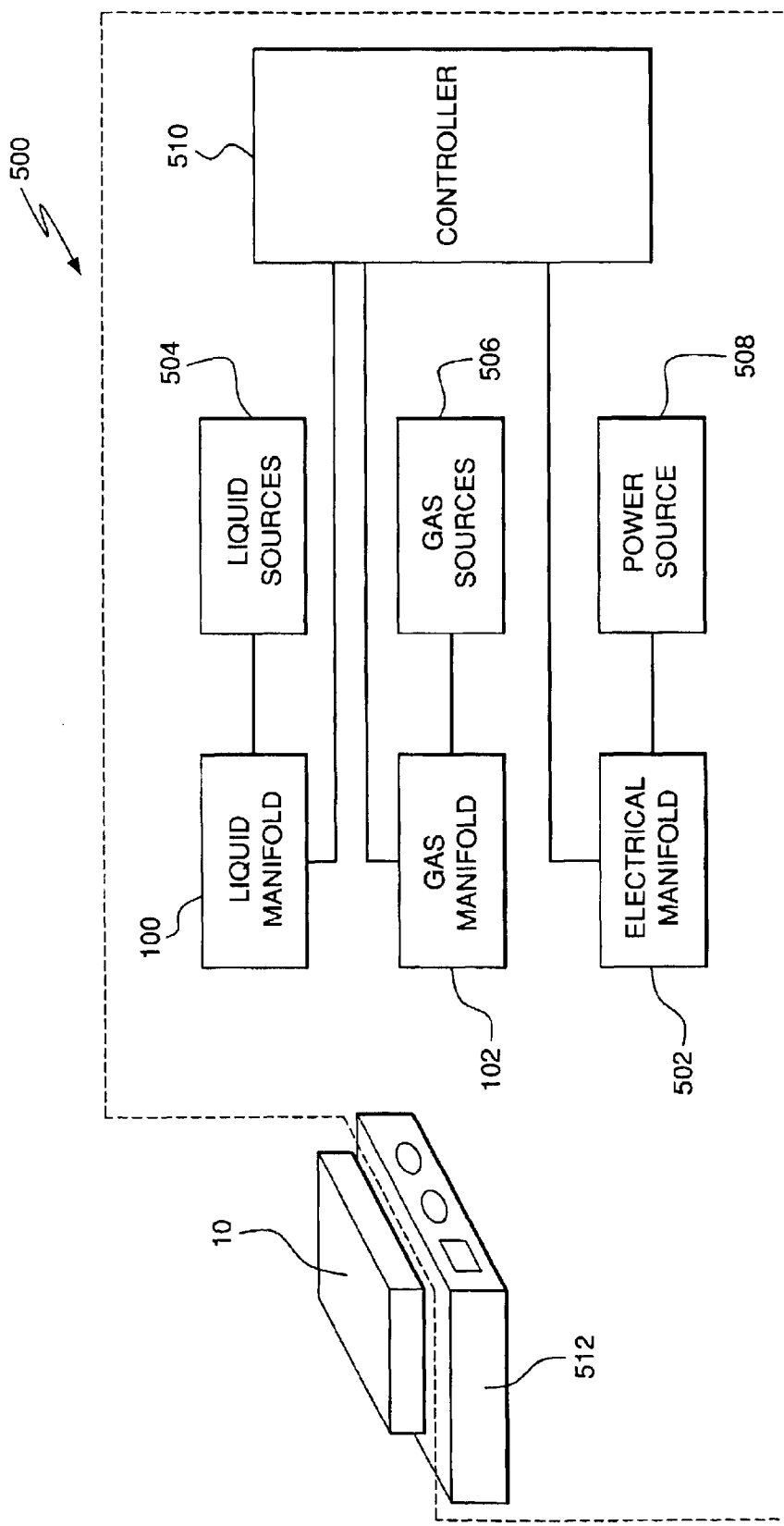
FIG. 8 is a schematic representation of an apparatus according to the present invention.

Each cassette or multiple-cassette stack connects to the apparatus through a set of liquid, gas and electrical manifolds that are controlled by the apparatus. FIG. 8 schematically represents one embodiment of the apparatus 500 with the liquid, gas and electrical manifolds 100, 102, 502, associated supply sources 504, 506, 508, and a controller 510. Also shown is a docking station 512 which receives a cassette 10.

Figure 6B:
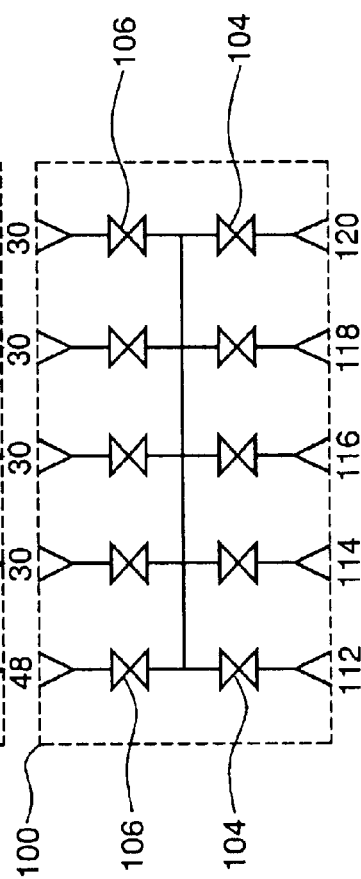
FIG. 6 is a schematic representation of liquid and gas manifold systems for use in an apparatus according to the present invention.
Figure 6A:
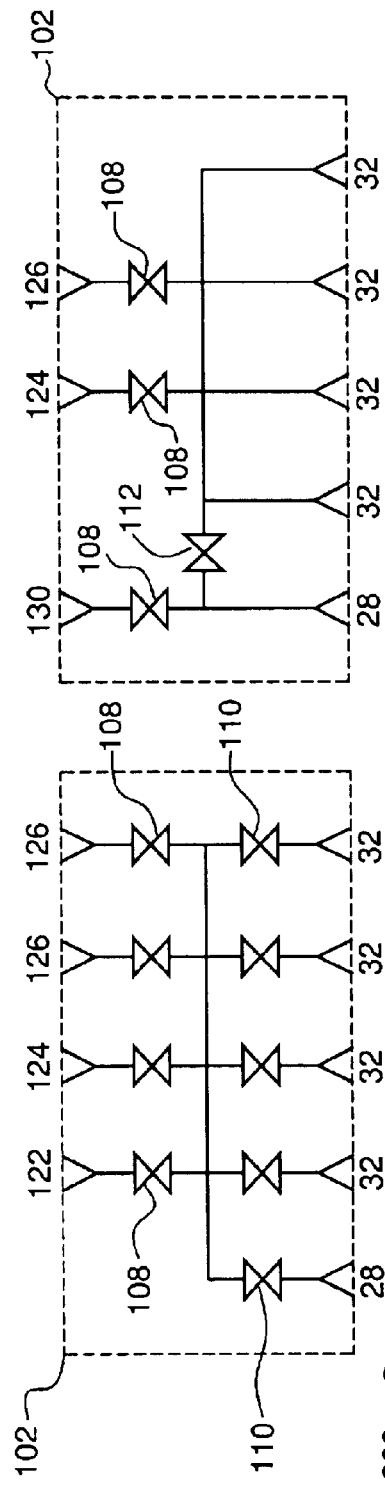

Referring to FIG. 6A, one embodiment of a liquid manifold 100 and of gas manifold 102 is shown. The supply/exhaust ports 30 and 48 and vent ports 28 and 32 on cassette 200 are numbered for illustrative purposes as in FIGS. 3 and 5. If some of the ports of cassette 200 are connected internally and/or if substrate reservoir 46 is absent, then some of the ports and valves shown in FIG. 6A are not needed. Also, if the cassette is only for 1D separation, only two buffer reservoir supply/exhaust ports 30/vent ports 32 are needed.

As shown in FIG. 6A, the liquid manifold 100 includes first and second sets of valves 104, 106, respectively which control flow of liquids between the apparatus and the cassette. More particularly, the each of the valves 104 in the first set controls a different liquid from a reservoir or source, such as a first buffer container (port 112), a second buffer container (port 114), a wash solution container (port 116), a liquid waste container (port 118) or a staining dye solution container (port 120). The second set of valves 106 selects whether the apparatus is connected to the supply/exhaust port of the substrate reservoir 46 (port 48), the first dimension buffer reservoirs 16 (the first two ports 30) or the second dimension buffer reservoirs 16 (the second two ports 30). The arrangement shown in FIG. 6A for liquid manifold 100 may be modified to take into account the fact that not all liquid paths are useful for a given process. For example, the first buffer may not need to be supplied to the second dimension buffer reservoirs 16, or the staining dye solution may need to be supplied only to substrate reservoir 46. The fluid routing can be may be simplified in the appropriate manner to achieve this.

It should be readily apparent that the liquid manifold 100 can connected to more than one container of each source in order to provide uninterrupted supply of the necessary liquid. Other types of liquids may be used as desired or necessary. Hence, this manifold arrangement permits different types of samples (e.g., proteins and nucleic acids) which require different substrates and/or buffers and/or post-separation treatment to be separated without having to segregate them and switch containers. By using suitable identifying indicia on each cassette or substrate, the apparatus can be programmed to switch separation protocols automatically when a different type of separation is needed for a specific sample or, for small numbers of separations, as commanded by the operator.

Referring now to the gas manifold, third and fourth sets of valves 108, 110, respectively, are used to control flow of gas between the apparatus and the cassette. More specifically, the third set of valves 108 are used to control whether cassette 200 is connected to a pressurization source (port 122), or a gas recovery system that is either depressurized (port 124) or at atmospheric pressure (first port 126), or directly to the atmosphere (second port 126). The fourth set of valves 110 are used to control whether the apparatus is connected to the vent port of the substrate reservoir 46 (port 28), the first dimension buffer reservoirs 16 (first two ports 32), or the second dimension buffer reservoirs 16 (the second two ports 32). For example, when first filling substrate reservoir 46 with first buffer, ports 48 and 112 are connected by opening the corresponding valves 104 and 106 (liquid supply side) and port 28 is connected to either port 124 or port 126 by opening the corresponding valves 108 and 110 (venting side). When substrate reservoir 46 is full, the corresponding valves 104 and 106 are closed while the corresponding valves 108 and 110 valves remain open. To discard the first buffer from substrate reservoir 46, the corresponding valve 106 is reopened and valve 104 corresponding to port 118 (liquid waste) is opened. Preferably, during any separation, all gas manifold valves are kept open and only the liquid manifold valves connecting the operating buffer reservoirs to the apparatus are closed. For example, during a first dimension separation, both substrate reservoir 46 and second dimension buffer reservoirs 16 remain connected to the liquid waste system (port 118) to prevent any accumulation of buffer that enters those reservoirs from first buffer reservoirs 16 through the substrate 22 or otherwise.

Manifolds 100 and 102 are readily modified to accommodate more and less complex supply/exhaust and vent modalities. For example, if the vent openings of reservoirs 16, 46 all connect inside cassette 200 to a single vent port (e.g., port 28), then there is no need for any of the fourth set of valves 110. In that case, if transfer of buffer from substrate reservoir 46 to buffer reservoirs 16 is desired, a new valve 130 is used, as shown in FIG. 6B. As an example of the use of this arrangement, if valves 104 and 106 connecting port 112 to port 48 are open, first buffer is introduced into the substrate reservoir 46, while venting takes place with valve 130 and the valve 108 connecting port 28 to either port 124 or port 126 (gas recovery system) also being open. When substrate reservoir 46 is full, the corresponding valve 104 is closed. After the substrate is saturated with first buffer, valve 130 is closed in order to permit selective pressurization of substrate reservoir 46, the valves 106 connecting port 48 (substrate reservoir 46) to the first two ports 30 (first dimension buffer reservoirs 16) are opened, and the valve 108 connecting port 28 to port 122 (gas pressurization system is opened. In this manner, pressurization of reservoir 16 transfers any first buffer remaining in substrate reservoir 46 to first dimension buffer reservoirs 16.

All method embodiments above can be modified to permit the use of a different buffer in each operating buffer reservoir by supplying and exhausting each buffer throughout the duration of each separation step, either continuously or in pulsed fashion, so as to maintain a buffer gradient in the substrate during the entire separation step. This can be done by exhausting buffer through the "vent" port and not through the "supply/exhaust" port of each buffer reservoir. For example, for each one of the buffer reservoirs 16, supply of buffer takes place through port 30 and exhaust takes place through port 32, or vice versa. This flow-through approach to supplying and exhausting liquids to and from the various reservoirs is, of course, applicable even if the same buffer is used in both buffer reservoirs. For example, if the capacity of the buffer reservoirs is made too small to sustain the entire separation and fresh buffer needs to be admitted in the course of the separation. Preferably, the same waste system accepts both liquid and gas waste, in which case there is no need to modify "gas" manifold 102, otherwise an additional valve and port connecting to a separate liquid waste container can be readily incorporated, or one of the two ports 126 shown in FIG. 6A may be used for that purpose.

On-off valves 104, 106, 108 and 110 in manifolds 100 and 102 may be subminiature electrically actuated valves widely used in liquid chromatography and other applications. For example, subminiature electrical solenoid valves, manifold-mountable with 7 mm center-to-center spacing, actuated by standard logic control signals, and rated for at least 250 million actuations, can be obtained from the Lee Company (Westbrook, Conn.). It is also contemplated that actuation of the valves may be by conventional mechanical, pneumatic or hydraulic systems. It is further contemplated that each set of onoff valves may be replaced by a single multi-port valve, rotary or other type, or by miniature electrically actuated pumps. Also, one or more valves 106 and/or 110 may be incorporated into the cassette itself (rather than in manifolds 100 and/or 102). Control of such cassette mounted valves is also preferably provided by the apparatus.

The volume of liquid delivered to each reservoir is preferably controlled by incorporating liquid float shut-off valves at each vent opening, by timing each valve's open state and shutting off flow based on the flow rate, or by using conventional metering pumps or valves instead of on-off valves. Each manifold is preferably of the commonly used "ant farm" type, which permits tight packing of valves and reduces dead liquid volume to a minimum.

The electrical manifold incorporated in the apparatus preferably includes two electrical terminals for connection to the voltage supply and an optional separate ground connection, a high-voltage, 4-pole double-throw, solid-state relay (or two separate 2-pole double-throw relays) for switching the voltage connection between first and second dimension electrodes, and one electrical contact for each electrode. Preferably, the relay(s) is/are actuated by standard logic control signals and is/are normally open with respect to all electrodes. Alternatively, two separate programmable power supplies or a single dual-output programmable power supply may be used instead of the relay(s). Optionally, the electrical manifold may also include diagnostic contacts that serve to register the presence of the cassette with an apparatus interlock system that prevents fluid and voltage supplies from being activated if a cassette is not present or, alternatively, register which type of cassette (e.g., 1D or 2D) is docked with the apparatus control system.

All of the cassette embodiments described above can be modified so that one or more of the liquid supply/waste containers are incorporated into the cassette itself (rather than being incorporated into the apparatus or otherwise connected to it). By way of illustration, referring to FIG. 6A, if the first buffer supply container is incorporated into the cassette 200 in addition to the five reservoirs shown, then port 112 in liquid manifold 100 connects to a corresponding additional port in cassette 200 (rather than, as shown, to a first buffer supply container incorporated into the apparatus or otherwise connected to it). The additional port would be equipped with a shut-off valve that opens upon docking.

With the modifications described in the preceding paragraph, the valve arrangement in and the liquid routing through manifold 100 remains unchanged other than the liquid source/destination being in the cassette rather than in the apparatus. Also, for one or more of the supply/waste containers that are incorporated into the cassette, the corresponding valve 104 may also be incorporated into the cassette together with the corresponding liquid routing channels and, as described above, one or more valves 106 and/or 110. By way of illustration, referring to FIG. 6A, if the first buffer supply container is incorporated into the cassette 200, then the valve 104 associated with port 112 may also be incorporated into the cassette. If the channels connecting the first buffer container to the buffer reservoirs 16 are also incorporated into the cassette with a valve 106 in each of those channels, then the supply/exhaust of first buffer becomes entirely internal to the cassette.

Multiple single cassettes may be operated simultaneously via a single set of liquid and gas manifolds, without stacking as described above, simply by interposing a multi-port line between the cassettes and each manifold so that each port on a manifold connects in parallel to multiple cassette-docking ports on the line. In order to permit operation with fewer cassettes than the number of cassette-docking ports in each multi-port line, each cassette-docking port is preferably equipped with a shut-off valve that opens only when a cassette is docked on it. For example one of ports 48 on liquid manifold 100 may connect to a line that has ten cassette-docking ports 48 on it, each of which is intended to connect to a substrate reservoir 46 of a different cassette. If only two cassettes are docked, then eight of the cassette-docking ports 48 in the line remain closed. With respect to the electrical connections in this arrangement, each contact in the single electrical manifold connects to an electrically conducting bus to which the corresponding electrical contact in each cassette connects. This type of arrangement differs from the parallel cassette stacking arrangement described above in that the fluid and electrical connections between the cassettes are now external to the cassettes, but its operation is otherwise the same.

Figure 7:
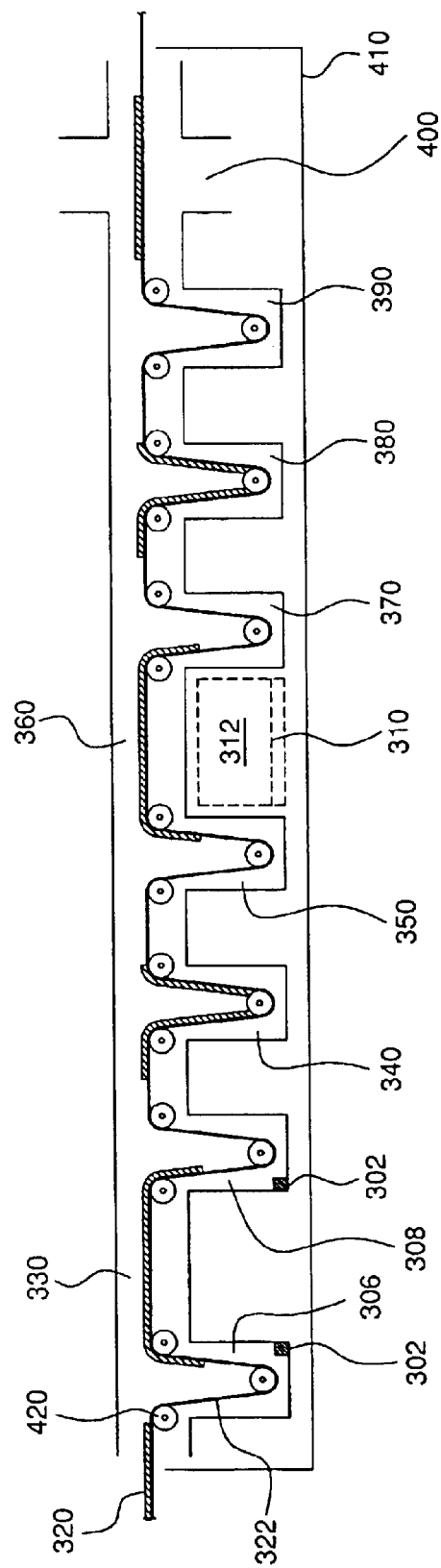
FIG. 7 is a schematic representation of a 2D cassette using a continuously moving roll or fan-fold substrate.

It is also contemplated that each step in the process, i.e., the first dimension separation, the second dimension separation, and the post-separation treatment, takes place in-line, at a different point along the path of a continuously moving roll or fan-fold substrate. FIG. 7 illustrates one schematic representation of a cassette embodiment for use with this in-line method. First dimension electrodes 302 and first dimension buffer reservoirs 306, 308 are perpendicular to the plane of the figure, while second dimension electrodes 310 and second dimension buffer reservoirs 312 (shown by dashed lines) are in front of and behind the plane of the figure.

A sample on substrate 320 passes through the several sections of the process. The substrate 320 enters the first dimension buffer reservoir 306 where the substrate 320 is saturated with first buffer. The substrate 320 is conveyed on a conveyor or substrate support 322 to a first dimension separation region 330. The substrate is then conveyed through the first dimension buffer reservoir 308, followed by an optional first rinse reservoir 340. The substrate is then transferred to a substrate reservoir 350 where the substrate 320 is saturated with second buffer, and then through the second buffer reservoirs 312 containing second dimension electrodes 310 and spanning second dimension separation region 360. The conveyor transports the substrate optionally through a second wash reservoir 370 and/or dye solution reservoir 380 followed by an optional third wash reservoir 390. Lastly, if desired, the substrate may be conveyed through a drying chamber 400. In the 1D variant (not shown), second dimension electrodes 310 and buffer reservoirs 312, second dimension separation region 360, and second wash reservoir 370 are not needed. A housing 410 may be incorporated below the conveyor to catch any leaking liquids.

FIG. 7 shows substrate 320 traveling under rollers 420 inside each reservoir, which cause the substrate to dip into the liquid in that reservoir. Not shown is an arrangement in second dimension separation region 360 that causes the edges of substrate 320 to bend down and dip into the buffer in second buffer reservoirs 312, similar to the arrangement shown in FIG. 1D. The liquid levels are below the height at which substrate 320 enters and exits the cassette (and passes from one reservoir to the next within the cassette). Therefore, there is no need for fluid-tight reservoirs thus simplifying the cassette. Alternatively, a substantially fluid-tight cassette is obtained by placing, at the boundaries between reservoirs and regions within the cassette, and at the cassette entry and exit points, slits between flexible blades that permit travel of substrate 320 but provide substantially fluid-tight separation between the various sections of the cassette and between the cassette and the outside. In this case, there is no need for rollers 420 inside each reservoir.

In the embodiment shown in FIG. 7, the liquids in the various reservoirs are supplied and removed in a continuous stream, and the voltage is continuously applied to all electrodes. The speed of continuous travel of substrate 320 is selected so that the time it takes for a particular sample to pass between electrodes is equal to the desired separation time. For example, if the substrate roll is 10 cm wide, all electrodes are 10 cm long, and the desired separation time is 5 minutes, then substrate 320 travels at the rate of 2 cm per minute. This embodiment is, thus, capable of performing 12 automated 2D separations per hour (including dye staining), with the samples placed on substrate 320 by a robotic pipette located ahead of the cassette. For 1D separations, a robotic multi-tip pipette may be used to place multiple samples simultaneously across the width of the substrate. If an 8-tip robotic pipette is used, this 1D variant of the method is capable of performing 96 automated separations per hour (including dye staining). The separation results can be examined in-line by an automated reading and analysis device located downstream from the cassette.

The apparatus of the invention includes an electronic control unit that serves to initiate and terminate each step of the method of the invention, whether automatically under computer control for the entire sequence of steps (preferably) or by action of the operator for each step or series of steps. The actions provided by the electronic control unit include, for example, sending a logic control pulse or signal to (1) a liquid valve in order to open it, (2) an electrical relay in order to switch the voltage from one pair of electrodes to the other, (3) a latch in order to lock a cassette during a separation, (4) a positioning mechanism to fetch substrates and insert them into cassettes, or (5) a mechanism that opens and closes the cassette. A user interface allows the operator to initiate and terminate a step or series of steps manually, or preferably to program and initiate complete separation protocols (i.e., particular method implementations). A computer controls the electronic control unit, in addition to communication with the user interface, stores separation protocols, barcode or other identifier reader information and sample information provided by the operator or by a computer data file, and communicates with external devices such automated cassette/substrate stackers and loaders, robotic pipettes, and automated reading and analysis systems that examine separation results. Alternately, the computer may be incorporated into the electronic control unit. The computer/electronic control unit may be any conventional device, such as a microprocessor, signal processor and the like. The control unit and/or computer preferably includes a storage medium, such as a hard drive, for storing operational protocol.

The apparatus of the invention is preferably constructed to accept interchangeable modular docking stations that plug into a common base. As discussed above, the docking station provides an interface between a cassette and the apparatus so as to permit easy engagement between the two. The docking station preferably includes fluid manifolds and an electrical manifold for interfacing between the connections on the cassette and the manifolds in the apparatus. The interface includes a series of automatic quick connects that mate with complementary connects on the cassette. Suitable quick fluid and electrical connections are readily available. Those skilled in the art would be capable of selecting appropriate connections for transmitting fluids and electricity in accordance with the present invention.

It may be desirable to incorporate the apparatus manifolds directly into the docking station, although such an arrangement is not preferable. In light of the different types of cassettes that can be used, it is desirable to fabricate the docking station such that it can accept a wide variety of cassette types. There may, however, be situations where a single docking station cannot accommodate all the different cassette types contemplated for use in the apparatus. As such, it is also contemplated that different docking stations may be fabricated that can be used in the apparatus, each docking station itself being capable of interfacing with a different set of cassettes types. Thus, the same docking station may accept 10 cm cassettes as well as 20 cm cassettes if the layout of the ports and contacts is the same for both types of cassettes. Alternately, each type of cassette may require a different type of docking station. Of course, since cassette types may differ in the number of ports and/or contacts, e.g., a 1D cassette will have fewer ports and contacts than a 2D cassette, it may be more economical for a 1D docking station to be fabricated that includes the minimum number of contacts and valves that are required for docking with a 1D cassette. This reduces the cost of the docking station. Also, edge-docking cassettes and face-docking cassettes may require different types of docking stations (or a docking station that can accept both types of cassettes).

In such a modular arrangement it is important for the apparatus' controller to be able to identify the type of docking station(s) in place and, for that docking station(s), the type(s) of cassette(s) that is/are docked. This permits the apparatus to "activate" and "deactivate" certain fluid lines and electrical lines depending on the cassette and/or docking station being used. One system that is contemplated for accomplishing this is by providing each cassette and docking station with a specific identifier. The identifier may be any conventional system used for identifying a component, such as a set of pins and jumpers, a bar code or a computer chip. The apparatus (or docking station) includes a reader that scans the identifier (in the case of readable identifiers), an electrical interface that communicates with the identifier (in the case of pins or chips) or any other type of identification system which provides a signal indicative to the identifier, e.g., a mechanical actuation system. The controller receives the signal indicative of the identifier and determines which docking station and cassette is/are in use (by comparison of the identifier with stored values). The operational protocols that are compatible with the particular cassette/docking station combination are then selected by the controller. In this manner, the same apparatus can accommodate multiple types of cassettes and docking stations without the necessity of reprogramming. Also, if the apparatus is capable of running multiple cassettes at the same time, the present invention permits the apparatus to associate different protocols for different docking stations automatically. It is also contemplated that the identification may be provided by a transmitted signal, such as an RF or IR signal, which is provided to the apparatus automatically by the docking station when it is connected to the apparatus (or automatically by the docking station when a cassette is inserted.) The controller receives the signal and selects the appropriates set(s) of protocol associated with the docking station/cassette.

Similarly, it is also contemplated that fluid supply/waste containers may advantageously include an identifier that allows the controller to determine which type of fluid is associated with a particular fluid supply/waste line, so that the controller may actuate the appropriate valves in order to deliver the desired fluid, without requiring that a particular container be attached to a particular line. This embodiment of the invention eliminates the need for the valves in FIG. 6A to be associated with particular fluid sources. Instead, the valves would all be inactive until a container is connected. At that point, the controller would receive a signal indicative of the identifier associated with the container. The controller would then select a valving protocol for controlling the first and second sets of fluid valves 104, 106 in light of where the fluid source is located. This aspect of the invention also permits the use of multiple sources of the same liquid, allowing the controller to select which source to use. For example, several containers of buffer may be connected to multiple valves. The controller would select one container to operate as the buffer source. When that container runs out of buffer, the controller could automatically switch to the second container as the buffer source (and at the same time provide a visual or audible signal to the operator that the first buffer container is empty.)

The modularity of the present invention is not limited to the docking station, cassettes and fluid containers. It is also contemplated that the manifolds may also be modular so as to permit different manifold arrangements to be used in the apparatus. As with the other modular components, the manifolds would include an identifier or identification device which allows the controller to identify the particular manifold. Thus, manifolds with different valving arrangements could be used which have different numbers of conduits for supplying/dispensing fluid, or different numbers of manifolds (for cases where additional docking stations are being added to the system.)

The modular system described above provides a very versatile and robust system which is capable of growing as electrophoretic procedures evolve.

The above-described identification techniques for the various modular systems is not limited to the structure of the apparatus and cassette but also includes the novel invention of an electrophoresis substrate that includes an identifier. As with the embodiments described above, an identifier incorporated into or associated with the substrate can assist in defining the appropriate program parameters for use in controlling the electrophoretic process. When the substrate is received by either the cassette or the apparatus, the cassette or apparatus senses or otherwise receives information related to the substrate which is then used by the cassette/apparatus for programming and or controlling certain steps of the electrophoresis process.

By way of example, and by no means limiting, the identifier may provide information regarding the substrate, such as, the type, shape and/or thickness of the substrate. Alternatively or additionally, the identifier may provide information regarding the type and number of samples being tested (e.g., the number and/or location of active wells, the sample type within each well) It is further contemplated that the identifier can provide information on the type of electrophoretic process to be run (e.g., 1D or 2D). The information received can then be used to tailor the electrophoretic process to the particular substrate.

In yet another embodiment, the substrate identification may be used for selecting the appropriate type of substrate to use for the sample being tested. For example, if the sample is a nucleic acid, a nylon substrate would be selected for use. The type of substrate may also be used to select the appropriate buffer solution and/or reservoirs that are active.

It is contemplated that the identification devices may be any of a number of different types of devices. For example, the identifier may be a dye in a portion of the substrate that is sensed or otherwise detected by the apparatus/cassette. Alternatively, the identifier may be an identification code (e.g., bar code, pattern, etc.), a specific pin-out configuration, a prescribed shape and/or configuration of the substrate, backing or frame (e.g., cross-shaped or surface anomaly), a computer memory chip or other identification means. It is contemplated that the identification devices may be disposed on or in the substrate or a backing or frame which supports the substrate. Those skilled in the art would readily appreciate the diverse identification devices (both passive and active) which can be used with either the substrate or the substrate backing or frame in light of the teachings provided herein.

In one embodiment, when the substrate is placed within a cassette, the cassette reads, receives or detects/senses the substrate identifier and provides the information to the apparatus and/or computer controller. The apparatus and/or controller use that information to configure the electrophoresis process (e.g., length/type of program, type of buffer, etc.) Alternatively, the apparatus/controller may read/detect the information from the substrate identifier directly from the substrate or its backing or frame.

As discussed above, it is contemplated that the substrate itself may be specifically tailored to operate with the cassette in an electrophoresis system. For example, as described above, the substrate itself may be cross-shaped with the "legs" of the substrate extending into the reservoirs. This shape is beneficial for several reasons. First, it minimizes the amount of substrate material (e.g., gel) that is needed. Second, the removed corners permit ports and drains that are part of the cassette to pass from the top to the bottom of the cassette without interfering with the substrate. Alternate substrate configurations include substrates with notches and cut-cuts. The cut-outs can be formed on the corners, edges or anywhere else that does not adversely effect the electrophoretic process in the substrate.

It is also contemplated that a substrate and backing combination can be used to mount to the cassette. For example, referring to FIG. 4C, the substrate 22 may be sold or provided in combination with a backing that includes the substrate support 24, the gasket seal 68 and a thermal conductor 60, such as the heat sink (cooling fins). The substrate support is preferably made from or includes an electrical insulator to prevent or inhibit electrical conduction between the buffer and/or gel and the thermal conductor. Alternatively, a separate electrically insulating layer can be incorporated on the substrate support or the thermal conductor. The substrate and backing would be configured to mate with or be received in an opening in the base 14 of the cassette 10. A latch or other conventional securing mechanism would be used to attach the backing to the base 14.

While in many of the above-embodiments the cassette included a reservoir on either end, it is also contemplated that the reservoir may be located outside of the cassette or eliminated all together. In this embodiment, a flow of buffer is channeled directly into the side of the substrate. The pressure from the buffer against the substrate would cause the buffer to permeate through the substrate and out the opposite side. Alternatively, the buffer is allowed to flow outside the substrate and along one its faces, and from there permeate through the substrate. Thus, a continuous flow of buffer can be used in the electrophoretic process.

The present invention may be embodied in other specific forms without departing from the spirit or essential attributes thereof and, accordingly, reference should be made to the appended claims, rather than to the foregoing specification, as indicating the scope of the invention.

What is claimed is:

1. A cassette for use in an electrophoresis apparatus, the cassette having an upper portion and a lower portion, the cassette comprising:
   at least two liquid reservoirs formed in the cassette spaced apart from one another, each reservoir being adapted to receive a liquid;
   a substrate support located between the liquid reservoirs;
   at least one port in fluid communication with at least one of the reservoirs and extending to an external surface of the cassette;
   at least one electrode located within each liquid reservoir;
   at least one electrical contact located on an external surface of the cassette and electrically connected to the at least one electrode so as to permit current to pass between the electrical contact and the electrode; and
   an electrophoretic substrate disposed on the substrate support, the substrate including at least two opposed ends, each end extending into one of the liquid reservoirs.

2. The cassette according to claim 1, wherein there are four liquid reservoirs formed in the cassette, each reservoir being substantially orthogonal to the adjacent reservoir; wherein there are four electrodes and four contacts, one electrode in each reservoir, each electrode being electrically connected to a separate electrical contact located on an external surface; and wherein there are at least two ports for supplying and removing liquid and at least one port for venting gas, each liquid port providing fluid communication between an associated reservoir or an associated pair of non-adjacent reservoirs and an external surface of the cassette, the vent port(s) providing fluid communication between at least one reservoir and an external surface of the cassette for passage of gas.

3. The cassette according to claim 1, further comprising a heat sink attached to the substrate support for providing heat transfer from the substrate support.

4. The cassette according to claim 1, wherein the substrate support is removably attached to the lower portion of the cassette.

5. A cassette according to claim 1, wherein the upper portion includes a cover and the lower portion includes a body, the cover being attached to the body with a seal so as to form a substantially liquid tight seal between the cover and the body of the cassette to prevent leakage of buffer during use, and wherein the seal is an integral portion of either the body or the cover.

6. A cassette according to claim 1, wherein the upper portion includes a cover and the lower portion includes a body, the cover being attached to the body with a seal so as to form a substantially liquid tight seal between the cover and the body of the cassette to prevent leakage of buffer during use, and wherein the seal is a separate component positioned between the body and the cover.

7. A cassette for use in an electrophoresis apparatus, the cassette having an upper portion and a lower portion, the cassette comprising:
 at least two liquid reservoirs formed in the cassette spaced apart from one another, each reservoir being adapted to receive a liquid;
 a substrate support located between the liquid reservoirs;
 at least one port in fluid communication with at least one of the reservoirs and extending to an external surface of the cassette;
 at least one electrode located within each liquid reservoir;
 at least one electrical contact located on an external surface of the cassette and electrically connected to the at least one electrode so as to permit current to pass between the electrical contact and the electrode; and
 wherein there are at least two ports formed in the upper portion of the cassette, each port extending between a liquid reservoir or pair of non-adjacent liquid reservoirs and an external surface of the cassette and adapted to permit flow of gas between the outside of the cassette and the liquid reservoir or pair of non-adjacent liquid reservoirs; wherein there are at least two ports formed in the lower portion of the cassette, each port extending between a reservoir or pair of non-adjacent liquid reservoirs and an external surface of the cassette and adapted to permit flow of liquid between the outside of the cassette and the liquid reservoir or pair of non-adjacent liquid reservoirs; and wherein there are at least two electrical contacts formed on the lower portion of the cassette, each contact being electrically connected to the electrodes in a separate liquid reservoir or pair of non-adjacent liquid reservoirs.

8. The cassette according to claim 7, wherein the upper portion of the cassette is spaced apart from the substrate support so as to define a substrate reservoir between the liquid reservoirs, which substrate reservoir is adapted to receive fluid; and wherein there is an additional port formed in the upper portion of the cassette which permits passage of fluid into and out of the substrate reservoir.

9. The cassette according to claim 8, wherein the additional port formed in the upper portion of the cassette permits flow of gas; and wherein there is a port formed in the substrate support which provides fluid communication between the substrate reservoir and an external surface of the cassette for passage of liquid out of the substrate reservoir.

10. The cassette according to claim 7, wherein the liquid ports and the at least one vent port all extend to one side or the bottom surface of the lower portion of the cassette; and wherein the electrical contacts are located at the same side or bottom surface of the lower portion of the cassette.

11. A cassette for use in an electrophoresis apparatus, the cassette having an upper portion and a lower portion, the cassette comprising:
 at least two liquid reservoirs formed in the cassette spaced apart from one another, each reservoir being adapted to receive a liquid;
 a substrate support located between the liquid reservoirs;
 at least one port in fluid communication with at least one of the reservoirs and extending to an external surface of the cassette;
 at least one electrode located within each liquid reservoir;
 at least one electrical contact located on an external surface of the cassette and electrically connected to the at least one electrode so as to permit current to pass between the electrical contact and the electrode; and
 wherein at least part of the upper portion of the cassette is movable with respect to the substrate support when the upper portion is engaged with the lower portion of the cassette.

12. The cassette according to claim 11, wherein the part of the upper portion of the cassette that is movable is a cover that spans over at least a portion of the substrate support; and wherein the movability of the cover is provided by a resilient member located between a peripheral edge of the cover and an edge of the upper portion of the cassette, the resilient member optionally biasing the cover away from the substrate support.

13. The cassette according to claim 11, wherein the entire upper portion of the cassette is movable with respect to the substrate support when the upper portion of the cassette is engaged with the lower portion of the cassette.

14. The cassette according to claim 13, wherein the movability is provided by a flexible gasket mounted between the upper portion and the lower portion of the cassette.

15. The cassette according to claim 13, wherein the movability is provided by a spring mounted between the upper portion and the lower portion of the cassette.

16. A cassette for use in an electrophoresis apparatus, the cassette having an upper portion and a lower portion, the cassette comprising:
 at least two liquid reservoirs formed in the cassette spaced apart from one another, each reservoir being adapted to receive a liquid;
 a substrate support located between the liquid reservoirs;
 at least one port in fluid communication with at least one of the reservoirs and extending to an external surface of the cassette;
 at least one electrode located within each liquid reservoir;
 at least one electrical contact located on an external surface of the cassette and electrically connected to the at least one electrode so as to permit current to pass between the electrical contact and the electrode; and
 wherein the liquid reservoirs are formed from at least one gasket located between the upper and lower portions of the cassette, the gasket having two spaced apart cut-outs, each cut-out defining at least a portion of a reservoir.

17. The cassette according to claim 16, wherein the at least one gasket has a third cut-out located above the substrate support and which cut-out defines a substrate reservoir adapted to receive a fluid.

18. The cassette according to claim 16, wherein the at least one gasket is attached to a section of the upper portion of the cassette.

19. A cassette for use in an electrophoresis apparatus, the cassette having an upper portion and a lower portion, the cassette comprising:
 at least two liquid reservoirs formed in the cassette spaced apart from one another, each reservoir being adapted to receive a liquid;
 a substrate support located between the liquid reservoirs;

at least one port in fluid communication with at least one of the reservoirs and extending to an external surface of the cassette;

at least one electrode located within each liquid reservoir; and at least one electrical contact located on an external surface of the cassette and electrically connected to the at least one electrode so as to permit current to pass between the electrical contact and the electrode;

wherein the upper portion includes a cover and the lower portion includes a body, the cover being attached to the body with a seal so as to form a substantially liquid tight seal between the cover and the body of the cassette to prevent leakage of buffer during use, wherein there are four liquid reservoirs formed in the cassette, each reservoir being substantially orthogonal to the adjacent reservoir; wherein there are four electrodes and four contacts, one electrode in each reservoir, each electrode being electrically connected to a separate electrical contact located on an external surface; and wherein there are at least two ports for supplying and removing liquid and at least one port for venting gas, each liquid port providing fluid communication between an associated reservoir or an associated pair of non-adjacent reservoirs and an external surface of the cassette, the vent port(s) providing fluid communication between at least one reservoir and an external surface of the cassette for passage of gas, and wherein the liquid ports and the at least one vent port all extend to one side or the bottom surface of the lower portion of the cassette, and wherein the electrical contacts are located at the same side or bottom surface of the lower portion of the cassette.

20. A cassette for use in an electrophoresis apparatus, the cassette having an upper portion and a lower portion, the cassette comprising:

at least two liquid reservoirs formed in the cassette spaced apart from one another, each reservoir being adapted to receive a liquid;

a substrate support located between the liquid reservoirs;

at least one port in fluid communication with at least one of the reservoirs and extending to an external surface of the cassette;

at least one electrode located within each liquid reservoir;

at least one electrical contact located on an external surface of the cassette and electrically connected to the at least one electrode so as to permit current to pass between the electrical contact and the electrode; and a porous layer disposed on the substrate support and extending into the liquid reservoirs.

21. A cassette for use in an electrophoresis apparatus, the cassette having an upper portion and a lower portion, the cassette comprising:

at least two liquid reservoirs formed in the cassette spaced apart from one another, each reservoir being adapted to receive a liquid;

a substrate support located between the liquid reservoirs;

at least one port in fluid communication with at least one of the reservoirs and extending to an external surface of the cassette;

at least one electrode located within each liquid reservoir;

at least one electrical contact located on an external surface of the cassette and electrically connected to the at least one electrode so as to permit current to pass between the electrical contact and the electrode; and wherein a removable attachment permits the substrate support to be slid laterally into the lower portion of the cassette.

22. A cassette for use in an electrophoresis apparatus, the cassette comprising:

a cover;

a body removably engageable to the cover;

at least two liquid reservoirs formed in the cassette between the cover and the body, the reservoirs being spaced apart from one another and adapted to receive a liquid;

a substrate support located in the body between the liquid reservoirs;

at least two liquid ports formed in the body, each liquid port extending between an associated liquid reservoir or pair of non-adjacent liquid reservoirs and an external surface of the body for channeling liquid between the reservoir or pair of non-adjacent reservoirs and the outside of the cassette;

at least two vent ports formed in the cover, each vent port extending between an associated liquid reservoir or pair of non-adjacent liquid reservoirs and an external surface of the cassette for channeling gas between the reservoir or pair of non-adjacent reservoirs and the outside of the cassette;

at least one electrode located within each liquid reservoir; and at least one electrical contact located on an external surface of the cassette, the contact being electrically connected to the electrodes so as to permit current to pass between the electrical contact and the electrodes.

23. The cassette according to claim 22, further comprising an electrophoretic substrate disposed on the substrate support, the substrate including at least two opposed ends, each end extending into one of the liquid reservoirs.

24. The cassette according to claim 22, wherein there are four liquid reservoirs formed in the cassette, each reservoir located substantially orthogonal to the adjacent reservoirs, wherein there are at least four liquid ports, vent ports and electrodes, each reservoir including at least one of the liquid ports, one of the vent ports and one of the electrodes, each electrode having an associated electrical contact.

25. The cassette according to claim 24, wherein the liquid ports and the vent ports extend to one side or a bottom surface of the body; and wherein the electrical contacts are located at the same side or bottom surface of the body.

26. The cassette according to claim 22, wherein a portion of the cover extends over and is spaced apart from the substrate support so as to define a substrate reservoir between the liquid reservoirs, the cassette further comprising a substrate liquid port formed in the body and a substrate vent port formed in the cover, the substrate liquid and vent ports extending between the substrate reservoir and an external surface of the cassette.

27. The cassette according to claim 26, wherein the liquid ports and the vent ports extend to one side or bottom surface of the body; and wherein the at least one electrical contact is located at the same side or bottom surface of the body.

28. The cassette according to claim 22, wherein at least a portion of the cover is mounted so as to be moveable with respect to the substrate support when the cover is attached to the body, the mounting optionally biasing the movable portion away from the substrate support.

29. The cassette according to claim 28, wherein the mounting is a flexible gasket between the movable portion of the cover and the remainder of the cover.

30. The cassette according to claim 28, wherein the mounting is a spring disposed between the cover and the body.

31. The cassette according to claim 22, wherein the liquid reservoirs are formed from at least one gasket located between the cover and body, the gasket having two spaced apart cut-outs, each cut-out defining at least a portion of a reservoir.

32. The cassette according to claim 22, further comprising a heat sink attached to the substrate support for transferring heat from the substrate support.

33. The cassette according to claim 22, further comprising a porous layer disposed on the substrate support and extending into the reservoirs.

34. The cassette according to claim 22, wherein the substrate support is removably attached to the body.

35. The cassette according to claim 22, wherein the removable engagement permits the substrate support to be slid laterally into the body.

36. A method for performing electrophoresis comprising the steps of:
providing a cassette having a cover and a body, the cassette including first and second liquid reservoirs located between the cover and body and spaced apart from one another by a substrate support, a substrate disposed on the support and having opposed ends located within each liquid reservoir, and electrodes located within each reservoir;
providing an electrophoretic apparatus having a docking station for receiving a cassette, a liquid buffer source, a waste container and a power source;
docking the cassette in the docking station of the apparatus such that the liquid buffer source and the waste container are in fluid communication with the reservoirs, and that the power source is in electrical communication with the electrodes;
placing a sample to be tested onto the substrate;
supplying buffer from the apparatus to the first and second reservoirs to fill the reservoirs to a height above the ends of the substrate located in the reservoirs;
saturating the substrate;
supplying power from the apparatus to the electrodes in the reservoirs to produce separation;
removing power from the electrodes;
channeling the used buffer from the reservoirs to the waste container in the apparatus; and
analyzing the substrate separation.

37. A method according to claim 36, wherein the step of supplying buffer to the reservoirs involves supplying a first amount of buffer into each reservoir to bring the level of the buffer to a first height within the reservoir; and wherein after the step of saturating the substrate, the method includes the step of removing a portion of the buffer from each reservoir to bring the level of the buffer to a second height within the reservoir.

38. A method according to claim 36, wherein the step of supplying buffer to the reservoirs involves channeling buffer through a central port above the substrate and permitting the buffer to flow over the substrate and into the reservoirs.

39. A method according to claim 36, wherein the step of supplying buffer to the reservoirs involves channeling buffer from the apparatus into the first and second reservoirs and over the substrate.

40. A method according to claim 36, wherein the cassette includes third and fourth buffer reservoirs located between the cover and body and spaced apart from one another by the substrate support, wherein the substrate has lateral sides which are located within the third and fourth buffer reservoirs, and wherein before the step of analyzing the substrate, the method comprises the step of
supplying buffer from the apparatus to the third and fourth reservoirs to fill the reservoirs to a height above the lateral sides of the substrate located in the reservoirs;
saturating the substrate;
supplying power from the apparatus to the electrodes in the third and fourth reservoirs to produce second dimension separation;
removing power from the electrodes; and
channeling the used buffer from the reservoirs to the waste storage in the apparatus.

41. The method according to claim 40, wherein prior to or during the step of supplying power to the third and fourth reservoirs, the method includes the step of removing any buffer that enters the first and second reservoirs.

42. A method according to claim 36, wherein after the step of saturating the substrate, the method includes the step of moving at least a portion of the cover toward the substrate to urge buffer located on the top of the substrate to flow into the reservoirs.

43. A method according to claim 42, wherein the step of moving at least a portion of the cover involves urging a hinged cover portion toward the substrate.

44. A method according to claim 42, wherein the step of moving at least a portion of the cover involves urging the cover down toward the body.

45. A method according to claim 36, wherein the cover includes a substrate cover section located above at least a portion of the substrate, the substrate cover being spaced apart from the substrate when the cover is attached to the body, the spacing defining a substrate reservoir above a substantial portion of the substrate, and wherein prior to the step of saturating the substrate, the method comprises the step of supplying buffer to the substrate reservoir.

46. A method according to claim 45, wherein after the step of saturating the substrate and prior to the step of supplying power, the method comprises the step of removing excess buffer from the substrate reservoir.

47. A method according to claim 36, wherein the substrate has lateral sides and wherein after the step of removing power from the electrodes the method comprises the steps of
opening the cassette;
rotating the substrate 90 degrees so that its lateral sides are positioned within the first and second reservoirs;
closing the cassette;
supplying power from the apparatus to the electrodes to produce second dimension separation; and
removing power from the electrodes.

48. A method for performing two dimensional electrophoresis comprising the steps of:
providing a cassette having a cover and a body, the cassette including a pair of spaced apart first dimension liquid reservoirs and a pair of spaced apart second dimension liquid reservoirs, the reservoir pairs being located between the cover and body and orthogonal to one another, a substrate support disposed between the liquid reservoirs in each pair, a substrate located on the support, the substrate having four sides, one side located within each liquid reservoir, and electrodes located within each reservoir;
providing an electrophoresis apparatus having a docking station for receiving a cassette, at least one liquid buffer source, a waste container and a power source;

docking the cassette in the docking station of the apparatus such that the liquid buffer source and the waste container are in fluid communication with the reservoirs, and that the power source is in electrical communication with the electrodes;

placing a sample to be tested onto the substrate;

supplying a first buffer from the apparatus to the first dimension liquid reservoirs to fill the reservoirs to a height above the ends of the substrate located in the reservoirs;

saturating the substrate with the first buffer;

supplying power from the apparatus to the electrodes in the first dimension liquid reservoirs to produce first dimension separation;

removing power from the electrodes;

channeling the used buffer from the first dimension liquid reservoirs to the waste container in the apparatus;

supplying a second buffer from the apparatus to the second dimension liquid reservoirs to fill the reservoirs to a height above the ends of the substrate located in the reservoirs;

saturating the substrate with the second buffer;

supplying power from the apparatus to the electrodes in the second dimension liquid reservoirs to produce second dimension separation;

removing power from the electrodes;

channeling the used buffer from the second dimension liquid reservoirs to the waste storage in the apparatus; and analyzing the substrate separation.

49. A method according to claim 48 wherein the step of supplying a first buffer to the reservoirs involves supplying a first amount of the first buffer into each of the first dimension reservoirs to bring the level of the buffer to a first height within the reservoir; and after the step of saturating the substrate with the first buffer, the method includes the step of removing a portion of the first buffer from each of the first dimension reservoirs to reduce the level of the buffer within each reservoir; and wherein the step of supplying a second buffer to the reservoirs involves supplying a first amount of the second buffer into each of the second dimension reservoirs to bring the level of the buffer to a first height within the reservoir; and after the step of saturating the substrate with the second buffer, the method includes the step of removing a portion of the second buffer from each of the second dimension reservoirs to reduce the level of the buffer within each reservoir.

50. A method according to claim 48, wherein the steps of supplying the first and second buffers to the associated reservoirs involves channeling the buffers through a central port above the substrate and permitting the buffers to flow over the substrate and into the reservoirs.

51. A method according to claim 48, wherein the step of supplying the first buffer involves channeling the first buffer from the apparatus into the first dimension reservoirs and over the substrate; and wherein the step of supplying the second buffer involves channeling the second buffer from the apparatus into the second dimension reservoirs and over the substrate.

52. The method according to claim 48, wherein prior to or during the step of supplying power to the electrodes in the first dimension reservoirs, the method includes the step of removing any buffer in the second dimension reservoirs; and wherein prior to or during the step of supplying power to the electrodes in the second dimension reservoirs, the method includes the step of removing any buffer in the first dimension reservoirs.

53. A method according to claim 48, wherein after each of the steps of saturating the substrate with the first and second buffer, the method includes the step of moving at least a portion of the cover toward the substrate to urge any buffer located on the top of the substrate to flow into the reservoirs.

54. A method according to claim 53, wherein the step of moving at least a portion of the cover involves urging a hinged cover portion toward the substrate.

55. A method according to claim 53, wherein the step of moving at least a portion of the cover involves urging the cover down toward the body.

56. A method according to claim 48, wherein the cover includes a substrate cover section located above at least a portion of the substrate, the substrate cover being spaced apart from the substrate when the cover is attached to the body, the spacing defining a substrate reservoir above a substantial portion of the substrate, and wherein prior to each of the steps of saturating the substrate with first and second buffers, the method comprises the step of supplying a buffer to the substrate reservoir.

57. A method according to claim 56, after the steps of saturating the substrate and prior to the steps of supplying power, the method comprises the step of removing excess buffer from the substrate reservoir.

58. A method for performing electrophoresis comprising the steps of:

providing a cassette having a conveyance system including a substrate support that extends from a first point to a second point, first and second liquid reservoirs located along the conveyance system between the first and second points, the reservoirs being spaced apart from one another, a plurality of substrates spaced apart from one another on the substrate support, each substrate having opposed ends, and electrodes located within each reservoir;

providing a liquid buffer source, a waste container and a power source;

placing a sample to be tested onto each substrate;

supplying buffer from the liquid buffer source to the first and second reservoirs to fill the reservoirs to a first height;

conveying the substrate support;

causing each substrate on the substrate support to pass into the first reservoir below the first height of liquid buffer to saturate the substrate with buffer;

causing the substrate to pass out of the first reservoir;

supplying power to the electrodes in the first and second reservoirs when the substrate is between the first and second reservoirs and while an end of the substrate is still within each reservoir;

removing power from the electrodes;

channeling the used buffer from the reservoirs to the waste container in the apparatus; and conveying the substrate to a location for post-separation treatment;

analyzing the substrate separation.

59. A method for performing two dimensional electrophoresis comprising the steps of:

providing a cassette having a cover and a body, the cassette including a pair of spaced apart liquid reservoirs located between the cover and body, a substrate support disposed between the liquid reservoirs, a substrate located on the support, the substrate having four sides, with two of the four sides being located within the liquid reservoirs, and electrodes located within each reservoir;

providing an electrophoresis apparatus having a docking station for receiving a cassette, at least one liquid buffer source, a waste container and a power source;

docking the cassette in the docking station of the apparatus such that the at least one liquid buffer source and the waste container are in fluid communication with the reservoirs, and that the power source is in electrical communication with the electrodes;

placing a sample to be tested onto the substrate;

supplying a first buffer from the apparatus to the liquid reservoirs to fill the reservoirs to a height above the ends of the substrate located in the reservoirs;

saturating the substrate with the first buffer;

supplying power from the apparatus to the electrodes to produce first dimension separation;

removing power from the electrodes;

disengaging the substrate from the cassette, rotating the substrate 90 degrees and replacing the substrate in the cassette such that the remaining two sides are in the reservoirs;

supplying power from the apparatus to the electrodes to produce second dimension separation;

removing power from the electrodes;

channeling the used buffer from the liquid reservoirs to the waste storage in the apparatus; and analyzing the substrate separation.

60. An electrophoresis apparatus comprising:
a docking station for receiving a cassette;
at least one electrical contact located at the docking station, the electrical contact being electrically connectable to a power source for supplying current to the contact;
at least one buffer source;
a waste storage container;
a liquid manifold including at least one dispenser located at the docking station, a plurality of conduits for conveying liquid from the at least one buffer source to the dispenser and for conveying waste from the docking station to the waste storage container, and at least one valve for controlling flow through the dispenser; and
a controller for controlling operation of the valves.

61. The apparatus of claim 60, wherein power source is a current supply; wherein there a plurality of electrical contacts located at the docking station; wherein the electrical connection is an electrical manifold which includes two electrical terminals for connection to the current supply, a switch connected to the terminals and the electrical contacts for switching the electrical connection between the contacts; and wherein the controller controls the switching of the switch.

62. The apparatus of claim 61, wherein the controller supplies logic control signals for controlling the switch.

63. The apparatus of claim 60, wherein the electrical manifold also includes a diagnostic contact mounted at the docking station; and wherein the controller is adapted to receiving signals from the diagnostic contact for recognizing a cassette in the docking station.

64. The apparatus of claim 63, wherein the controller controls the valves to prevent supply of fluid and current from the sources when there is no cassette detected in the docking station.

65. The apparatus of claim 60, further comprising a robotic pipette for dispensing samples into a docked cassette; and a storage container for holding samples until dispensed.

66. The apparatus of claim 60, further comprising a pressure applicator mounted adjacent to the docking station and adapted to contact a docked cassette for applying pressure to the top of bottom of the cassette to cause at least a portion of the cassette to move relative to the remainder of the cassette.

67. The apparatus of claim 60, further comprising a bar code reader positioned so as to read indicia formed on a cassette, the bar code reader supplying signals to the controller indicative of the indicia on a cassette.

68. The apparatus of claim 67, wherein the controller includes a plurality of stored electrophoresis process procedures, the controller selecting an appropriate process procedure based on the supplied signals from the bar code reader.

69. The apparatus of claim 60, further comprising an automated reading and analysis system for analyzing a substrate after separation.

70. The apparatus of claim 60, wherein there are a plurality of buffer sources; wherein the liquid manifold includes a plurality of valves for controlling flow from the buffer sources to the dispenser; and wherein controller selectively controls the opening and closing of the valves for controlling flow of liquid from the different buffer sources.

71. The apparatus of claim 70, wherein there are a plurality of dispensers; and wherein the controller selectively controls the opening and closing of the valves to control flow of liquid from the different dispensers.

72. The apparatus of claim 60, wherein there is a first set of valves and a second set of valves, the opening and closing of each valve in the first and second sets being controlled by the controller so as to control flow through the manifold.

73. The apparatus of claim 60, further comprising a wash solution source; and wherein the liquid manifold includes conduits for conveying wash solution from the wash solution source to the at least one dispenser.

74. The apparatus of claim 60, further comprising a dyeing solution source; and wherein the liquid manifold includes conduits for conveying dyeing solution from the dyeing solution source to the at least one dispenser.

75. An electrophoresis apparatus according to claim 60, further comprising at least one gas source; and a gas manifold including at least one dispenser at the docking station, at least one conduit for conveying gas between the gas source and the dispenser, and at least one valve for controlling flow through the dispenser.

76. The apparatus of claim 75, wherein there are a plurality of gas sources; wherein the gas manifold includes a plurality of valves for controlling flow between the gas sources and the dispenser; and wherein the controller selectively controls the opening and closing of the valves for controlling flow of gas between the different gas sources and the dispenser.

77. The apparatus of claim 76, wherein there are a plurality of dispensers; and wherein the controller selectively controls the opening and closing of the valves to control flow of gas through the different dispensers.

78. The apparatus of claim 76, wherein there is a first set of valves and a second set of valves, the opening and closing of each valve in the first and second sets being controlled by the controller so as to control flow through the manifold.

79. The apparatus of claim 76, wherein one of the gas sources is the atmosphere.

80. The apparatus of claim 76, wherein one of the gas sources is a pressurized gas source.

81. The apparatus of claim 76, wherein one of the gas sources is a depressurization source.

82. An electrophoresis apparatus comprising:
- a docking station for receiving a cassette;
- at least one electrical contact located at the docking station, the electrical contact being electrically connectable to a power source for supplying current to the contact;
- at least one buffer source;
- a waste storage container;
- a post separation solution source;
- at least one gas source;
- a liquid manifold including a plurality of dispensers at the docking station, a set of first conduits connected to the at least one buffer source, the waste storage container and the post-separation solution source;
- a first valve connected to each first conduit;
- a set of second conduits connected to each valve;
- a second valve connected to each second conduit;
- a set of third conduits, each third conduit connecting a second valve to a dispenser;
- a gas manifold including at least one dispenser at the docking station, at least one conduit for conveying gas between the at least one gas source and the dispenser, and at least one valve for controlling flow through the dispenser; and
- a controller for controlling operation of the valves.

83. The apparatus of claim 82, wherein there is a plurality of electrical contacts located at the docking station; wherein the electrical connection is an electrical manifold which includes two electrical terminals for connection to the power source, a switch connected to the terminals and the electrical contacts for switching the electrical connection between the contacts; and wherein the controller controls the switching of the switch.

84. The apparatus of claim 82, wherein the electrical manifold also includes a diagnostic contact mounted at the docking station; and wherein the controller is adapted to receiving signals from the diagnostic contact for recognizing a cassette in the docking station.

85. The apparatus of claim 84, wherein the controller controls the valves to prevent fluid and current from the sources when there is no cassette detected in the docking station.

86. The apparatus of claim 82, further comprising a robotic pipette for dispensing samples into a docked cassette; and a storage container for holding samples until dispensed.

87. The apparatus of claim 82, wherein the post-treatment solution source includes a dye solution.

88. The apparatus of claim 82, wherein the post-treatment solution source includes a wash solution.

89. The apparatus of claim 82, wherein there are a plurality of gas sources; wherein the gas manifold includes a plurality of valves for controlling flow between the gas sources and the dispenser; and wherein the controller selectively controls the opening and closing of the valves for controlling flow of gas between the different gas sources and the dispenser.

90. The apparatus of claim 89, wherein there are a plurality of dispensers; and wherein the controller selectively controls the opening and closing of the valves to control flow of gas through the different dispensers.

91. The apparatus of claim 89, wherein there is a first set of valves and a second set of valves, the opening and closing of each valve in the first and second sets being controlled by the controller so as to control flow through the manifold.

92. The apparatus of claim 89, wherein one of the gas sources is the atmosphere.

93. The apparatus of claim 89, wherein one of the gas sources is a pressurized gas source.

94. The apparatus of claim 89, wherein one of the gas sources is a depressurization source.

95. An electrophoresis apparatus comprising:
- at least two liquid reservoirs spaced apart from one another;
- a conveyance system for receiving a series of substrates, the conveyance system including a substrate support, the conveyance system adapted to transport the substrate support through at least one liquid reservoir;
- at least one electrode located in each liquid reservoir and electrically connectable to a power source for supplying current to the electrode; and
- at least one conduit for supplying buffer to at least one of the reservoirs.

96. A cassette for use in an electrophoresis apparatus, the cassette having an upper portion and a lower portion, the cassette comprising:
- a substrate support located within a substrate chamber;
- at least one inlet port in fluid communication with the substrate chamber and extending to an external surface of the cassette;
- at least one outlet port in fluid communication with the substrate chamber and extending to an external surface of the cassette;
- at least two electrodes located within the cassette, one electrode positioned so as to be within the flow path of a fluid passing through the at least one inlet port, and one electrode positioned so as to within the flow path of a fluid passing out the at least one outlet port; and
- at least two electrical contacts located on an external surface of the cassette, each electrical contact being electrically connected to an electrode so as to permit current to pass between the electrical contact and the electrode;
- wherein the upper portion includes a cover and the lower portion includes a body, the cover being attached to the body with a seal so as to form a substantially liquid tight seal between the cover and the body of the cassette to prevent leakage of buffer during use.

97. A method for performing electrophoresis comprising the steps of:
- providing a cassette having an upper portion and a lower portion and a substrate support located within a substrate chamber located between the upper and lower portions, at least one inlet port in fluid communication with the substrate chamber and extending to an external surface of the cassette, at least one outlet port in fluid communication with the substrate chamber and extending to an external surface of the cassette, at least two electrodes located within the cassette, and a substrate disposed on the support;
- providing an electrophoretic apparatus having a docking station for receiving a cassette, a liquid buffer source, a waste container and a power source;
- docking the cassette in the docking station of the apparatus such that the liquid buffer source is in communication with the at least one inlet and the waste container is in fluid communication with the at least one outlet, and that the power source is in electrical communication with the at least two electrodes;

placing a sample to be tested onto the substrate;

supplying buffer from the apparatus to the cassette;

saturating the substrate;

supplying power from the apparatus to the electrodes to produce separation;

removing power from the electrodes;

channeling the used buffer to the waste container in the apparatus; and analyzing the substrate separation.

98. A method according to claim 97, wherein before the step of analyzing the substrate, the method comprises the step of treating the substrate with a dyeing solution to facilitate analysis.

99. A method according to claim 97, wherein before the step of analyzing the substrate, the method comprises the step of removing the substrate from the cassette.

100. A method according to claim 97, wherein before the step of analyzing the substrate, the method comprises the step of performing post-separation treatment of the substrate to facilitate analysis.

101. A method according to claim 100, wherein the step of performing post-separation treatment includes the steps of staining the substrate while in the cassette, and rinsing the substrate.

102. A method according to claim 97, wherein before the step of analyzing the substrate, the method comprises the step of performing post-separation treatment of the substrate to facilitate analysis.

103. A method according to claim 102, wherein step of performing post-separation treatment includes the steps of staining the substrate while in the cassette, and rinsing the substrate.

104. A cassette for use in an electrophoresis apparatus, the cassette having an upper portion and a lower portion, the cassette comprising:

at least two liquid reservoirs formed in the cassette spaced apart from one another, each reservoir being adapted to receive a liquid;

a substrate support located between the liquid reservoirs;

at least one port in fluid communication with at least one of the reservoirs and extending to an external surface of the cassette;

at least one electrode located within each liquid reservoir; and at least one electrical contact located on an external surface of the cassette and electrically connected to the at least one electrode so as to permit current to pass between the electrical contact and the electrode;

wherein the upper portion includes a cover and the lower portion includes a body, the cover being attached to the body with a seal so as to form a substantially liquid tight seal between the cover and the body of the cassette to prevent leakage of buffer during use, and wherein the seal is flexible.

* * * * *